United States Patent
Mathis et al.

(10) Patent No.: US 10,513,698 B2
(45) Date of Patent: Dec. 24, 2019

(54) POTATOES WITH REDUCED COLD-INDUCED SWEETENING

(71) Applicant: CELLECTIS, Paris (FR)

(72) Inventors: Luc Mathis, Le Kremlin Bicetre (FR); Daniel F. Voytas, Falcon Heights, MN (US); Feng Zhang, Plymouth, MN (US); Benjamin Clasen, South St. Paul, MN (US); William Haun, St. Paul, MN (US); Thomas Stoddard, St. Louis Park, MN (US)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 14/653,604

(22) PCT Filed: Dec. 20, 2013

(86) PCT No.: PCT/IB2013/003222
§ 371 (c)(1),
(2) Date: Jun. 18, 2015

(87) PCT Pub. No.: WO2014/096972
PCT Pub. Date: Jun. 26, 2014

(65) Prior Publication Data
US 2016/0037742 A1 Feb. 11, 2016

Related U.S. Application Data

(60) Provisional application No. 61/745,003, filed on Dec. 21, 2012.

(51) Int. Cl.
| | | |
|---|---|---|
| *C12N 15/01* | (2006.01) | |
| *C12N 15/82* | (2006.01) | |
| *A01H 6/82* | (2018.01) | |

(52) U.S. Cl.
CPC ......... *C12N 15/01* (2013.01); *C12N 15/8245* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,001,768 B2 | 2/2006 | Wolffe |
| 7,013,219 B2 | 3/2006 | Case et al. |
| 7,067,722 B2 | 6/2006 | Fillatti |
| 7,070,934 B2 | 7/2006 | Cox, III et al. |
| 7,163,824 B2 | 1/2007 | Cox, III et al. |
| 7,189,691 B2 | 3/2007 | Hemenway |
| 7,220,719 B2 | 5/2007 | Case et al. |
| 7,262,054 B2 | 8/2007 | Jamieson et al. |
| 7,273,923 B2 | 9/2007 | Jamieson et al. |
| 7,285,416 B2 | 10/2007 | Choo et al. |
| 7,361,635 B2 | 4/2008 | Miller et al. |

(Continued)

FOREIGN PATENT DOCUMENTS

| | | |
|---|---|---|
| CN | 1618976 | 5/2005 |
| CN | 102558309 | 7/2012 |

(Continued)

OTHER PUBLICATIONS

2010, Draffehn et al, BMC Plant Bio., 10:1-15.*
Monma et al, 2005, J. Food Hyg. Soc. Japan, 46:79-85.*
Nakamura et al, 2013, Japanese Journal of Food Chemistry and Safety, 20:161-169.*
Bogdanove et al, 2011, Science, 333:1843-1846.*
U.S. Appl. No. 61/225,043, filed Jul. 13, 2009, Bonas et al.
"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).

(Continued)

*Primary Examiner* — Jason Deveau Rosen
(74) *Attorney, Agent, or Firm* — Fish & Richardson P.C.

(57) ABSTRACT

Materials and methods are provided for making *Solanum* varieties with decreased accumulation of reducing sugars and acrylamide in cold-stored potatoes, specifically, by making TALE-nuclease-induced mutations in genes encoding vacuolar invertase.

6 Claims, 4 Drawing Sheets
Specification includes a Sequence Listing.

(56) References Cited

U.S. PATENT DOCUMENTS

| | | | |
|---|---|---|---|
| 7,521,241 | B2 | 4/2009 | Choo et al. |
| 7,842,489 | B2 | 11/2010 | Arnould et al. |
| 8,420,782 | B2 | 4/2013 | Bonas et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,586,363 | B2 | 11/2013 | Voytas et al. |
| 8,697,853 | B2 | 4/2014 | Voytas et al. |
| 9,035,129 | B2 | 5/2015 | Bilyeu et al. |
| 9,198,365 | B2 | 12/2015 | Bilyeu et al. |
| 2001/0016956 | A1 | 8/2001 | Ward et al. |
| 2005/0064474 | A1 | 3/2005 | Umov et al. |
| 2007/0141038 | A1 | 6/2007 | Choulika et al. |
| 2009/0060921 | A1 | 3/2009 | Dickey et al. |
| 2009/0133158 | A1 | 5/2009 | Lahaye et al. |
| 2009/0271881 | A1 | 10/2009 | Arnould et al. |
| 2009/0305402 | A1 | 12/2009 | Liljedahl et al. |
| 2010/0132069 | A1 | 5/2010 | Lahaye et al. |
| 2010/0154081 | A1 | 6/2010 | Weterings et al. |
| 2010/0199386 | A1* | 8/2010 | Bhaskar ............ C12N 15/8218 800/284 |
| 2010/0199396 | P1 | 8/2010 | Higaki |
| 2011/0041195 | A1 | 2/2011 | Doyon |
| 2011/0129898 | A1 | 6/2011 | Doyon et al. |
| 2011/0136895 | A1 | 6/2011 | Gregory et al. |
| 2011/0145940 | A1* | 6/2011 | Voytas ................. C12N 9/22 800/13 |
| 2011/0158957 | A1 | 6/2011 | Bonini et al. |
| 2011/0167521 | A1 | 7/2011 | DeKelver et al. |
| 2011/0201055 | A1 | 8/2011 | Doyon et al. |
| 2011/0201118 | A1 | 8/2011 | Yang et al. |
| 2011/0203012 | A1 | 8/2011 | Dotson et al. |
| 2011/0207221 | A1 | 8/2011 | Cost et al. |
| 2011/0239315 | A1 | 9/2011 | Bonas et al. |
| 2011/0247089 | A1 | 10/2011 | Doyon |
| 2011/0265198 | A1 | 10/2011 | Gregory et al. |
| 2011/0269234 | A1 | 11/2011 | Doyon et al. |
| 2011/0287545 | A1 | 11/2011 | Cost et al. |
| 2011/0301073 | A1 | 12/2011 | Gregory et al. |
| 2012/0110685 | A1 | 5/2012 | Bonas et al. |
| 2012/0122205 | A1 | 5/2012 | Bonas et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2012/0246764 | A1 | 9/2012 | Hlubek et al. |
| 2012/0284877 | A1 | 11/2012 | Hlubek et al. |
| 2012/0324603 | A1 | 12/2012 | Hlubek et al. |
| 2013/0122581 | A1 | 5/2013 | Voytas et al. |
| 2014/0090116 | A1 | 3/2014 | Ainley et al. |
| 2014/0178561 | A1* | 6/2014 | Mathis ................ C12N 15/01 426/637 |
| 2017/0258024 | A1 | 9/2017 | Mathis et al. |

FOREIGN PATENT DOCUMENTS

| | | |
|---|---|---|
| CN | 102770539 | 11/2012 |
| EP | 0 242 246 | 10/1987 |
| EP | 2 206 723 | 7/2010 |
| EP | 2 392 208 | 12/2011 |
| EP | 2 562 260 | 2/2013 |
| WO | WO 1994/18313 | 8/1994 |
| WO | WO 1995/09233 | 4/1995 |
| WO | WO 2004/067736 | 8/2004 |
| WO | WO 2007/060495 | 5/2007 |
| WO | WO 2008/141806 | 11/2008 |
| WO | WO 2009/095793 | 8/2009 |
| WO | WO 2010/079430 | 7/2010 |
| WO | WO 2010/091018 | 8/2010 |
| WO | WO 2010/145846 | 12/2010 |
| WO | WO 2011/005998 | 1/2011 |
| WO | WO 2011/017293 | 2/2011 |
| WO | WO 2011/019385 | 2/2011 |
| WO | WO 2011/072246 | 6/2011 |
| WO | WO 2011/100058 | 8/2011 |
| WO | WO 2011/117249 | 9/2011 |
| WO | WO 2011/146121 | 11/2011 |
| WO | WO 2011/154393 | 12/2011 |
| WO | WO 2012/106105 | 8/2012 |
| WO | WO 2013/050155 | 4/2013 |
| WO | WO 2014/039692 | 3/2014 |
| WO | WO 2014/039702 | 3/2014 |

OTHER PUBLICATIONS

Alam and Sittman, "Characterization of the cytotoxic effect of a chimeric restriction enzyme, H1°-FokI," Gene Ther Mol Biol, 10:147-160, 2006.

Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.

Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.

Antony et al., "Rice xa13 recessive resistance to bacterial blight is defeated by induction of the disease susceptibility gene Os-11N3," Plant Cell, 22(11):3864-3876, 2010.

Antony, "Molecular basis of avrXa7 mediated virulence in bacterial blight of rice," [abstract of dissertation] Kansas State University, 99 pages, 2010.

Arimondo et al., "Exploring the cellular activity of camptothecin-triple-helix-forming oligonucleotide conjugates," Mol Cell Biol, 26:324-333, 2006.

Athinuwat et al., "Xanthomonas axonopodis pv. glycines soybean cultivar virulence specificity is determined by avrBs3 homolog avrXgl," Phytopathology, 99(8):996-1004, 2009.

Bai et al., "*Xanthomonas oryzae* pv. oryzae avirulence genes contribute differently and specifically to pathogen aggressiveness," Mol Plant Microbe Interact, 13(12):1322-1329, 2000.

Baker, "Gene-editing nucleases," *Nature Methods*, 2012, 9:23-26.

Ballvora et al., "Genetic mapping and functional analysis of the tomato Bs4 locus governing recognition of the Xanthomonas campestris pv. vesicatoria AvrBs4 protein," Mol Plant Microbe Interact, 14(5):629-638, 2001.

Belahj et al., "Plant genome editing made easy: targeted mutagenesis in model and crop plants using the CRISPR/Cas system," *Plant Methods*, 2013, 9:39.

Beretta et al., "Tethering a type IB topoisomerase to a DNA site by enzyme fusion to a heterologous site-selective DNA-binding protein domain," Cancer Res, 59:3689-3697, 1999.

Bethke and Busse, "Validation of a simple, colorimetric, microplate assay using amplex red for the determination of glucose and sucrose in potato tubers and other vegetables," *Am. J. Pot Res*., 2008, 85:414-421.

Beuselinck et al., "An Assessment of Phenotype Selection for Linolenic Acid Using Genetic Markers," *Crop Sci*, 47:747-750 (2006).

Bhaskar et al., "Suppression of the vacuolar invertase gene prevents cold-induced sweetening in potato," *Plant Physiol*., Oct. 2010, 154(2):939-948.

Bibikova et al., "Enhancing gene targeting with designed zinc finger nucleases," Science, 300(5620):764, 2003.

Bibikova et al., "Stimulation of homologous recombination through targeted cleavage by chimeric nucleases," Mol Cell Biol, 21(1): 289-297, 2001.

Bitinaite et al., "FokI dimerization is required for DNA cleavage," Proc Natl Acad Sci USA, 95:10570-10575, 1998.

Boch and Bonas. "Xanthomonas AvrBs3 family-type III effectors: discovery and function." Annu Rev Phytopathol, 48, 419-436, 2010.

Boch et al., "Breaking the code of DNA binding specificity of TAL-type III effectors," Science, 326:1509-1512, 2009.

Boch et al., "Molecular characterization of three AvrBs3-like effectors from the *Arabidopsis* pathogen Xanthomonas campestris pv.

(56) References Cited

OTHER PUBLICATIONS armoraciae," (abstract), XIV International Congress on Molecular Plant-Microbe Interactions, Quebec City, Canada, Jul. 19-23, 2009, 2 pages.
Bogdanove et al., "TAL effectors: Customizable Proteins for DNA Targeting," Science, 333: 1843-1846, 2011.
Bogdanove et al., "TAL effectors: finding plant genes for disease and defense," Curr Opin Plant Biol, 13:394-401, 2010.
Boller and He, "Innate immunity in plants: an arms race between pattern recognition receptors in plants and effectors in microbial pathogents," Science, 324:742-744, 2009.
Bonas et al., "Resistance in tomato to Xanthomonas campestris pv vesicatoria is determined by alleles of the pepper-specific avirulence gene avrBs3," Mol Gen Genet, 328: 261-269, 1993.
Bonas et al., "Genetic and structural characterization of the avirulence gene avrBs3 from Xanthomonas campestris pv. Vesicatoria," Mol Gen Genet, 218:127-136, 1989.
Bonas et al., "How the bacterial plant pathogen Xanthomonas campestris pv. vesicatoria conquers the host," Mol Plant Pathol, 1(1):73-76, 2000.
Bonas et al., "Resistance in tomato to Xanthomonas campestris pv vesicatoria is determined by alleles of the pepper-specific avirulence gene avrBs3," Mol Gen Genet, 238(1-2):261-269, 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.
Busk, "Regulatory elements in vivo in the promoter of the abscisic acid responsive gene rab17 from maize," Plant J, 11:1285-1295, 1997.
Büttner and Bonas, "Getting across—bacterial type III effector proteins on their way to the plant cell," EMBO J, 2002, 21(20):5313-5322, 2002.
Büttner et al., "Functional analysis of HrpF, a putative type III translocon protein from Xanthomonas campestris pv. vesicatoria," J Bacteriol, 184(9):2389-2398, 2002.
Büttner et al., "HpaB from Xanthomonas campestris pv. vesicatoria acts as an exit control protein in type III-dependent protein secretion," Mol Microbiol, 54(3):755-768, 2004.
Büttner et al., "Targeting of two effector protein classes to the type III secretion system by a HpaC- and HpaB-dependent protein complex from Xanthomonas campestris pv. vesicatoria," Mol Microbiol, 59(2):513-527, 2006.
Canteros et al., "A gene from Xanthomonas campestris pv. vesicatoria that determines avirulence in tomato is related to avrBs3," Mol Plant Microbe Interact, 4(6):628-632, 1991.
Carlson et al., "Targeting DNA With Fingers and TALENs," Mol Ther Nucl Acids, 1:e3, doi:10.1038/mtna.2011.5, 4 pages, 2012.
Cathomen et al., "Zinc-finger nucleases: the next generation emerges," Mol Ther, 16(7):1200-1207, 2008.
Cavalier et al., "Disrupting Two *Arabidopsis thaliana* Xylosyltransferase Genes Results in Plant Deficient in Xyloglucan, a Major Primary Cell Wall Component," *The Plant Cell*, 20:1519-1537 (Jun. 2008).
Cermak et al., "Efficient design and assembly of custom TALEN and other TAL effector-based constructs for DNA targeting," *Nucleic Acids Res.*, 2011, 39:e82.
Cermak et al., Poster and Abstract—"Engineered TAL effector nucleases: new tools for genome editing," Northwest Genome Engineering Consortium Workshop on Genome Engineering, 3 pages, 2010.
Chevalier et al., "Design, activity, and structure of a highly specific artificial endonuclease," Mol Cell, 10(4):895-905, 2002.
Choo et al., "In vivo repression by a site-specific DNA-binding protein designed against an oncogenic sequences," Nature, 372(6507):642-645, 1994.
Choulika et al., "Induction of homologous recombination in mammalian chromosomes by using the I-SceI system of *Saccharomyces cerevisiae*," Mol Cell Biol, 15(4):1968-1973, 1995.
Christian et al., "Targeting DNA double-strand breaks with TAL effector nucleases," *Genetics*, 2010, 186:757-761.
Christian et al., Poster and Abstract—"Fusions of TAL effectors to the FokI endonuclease confer site specificity in DNA cleavage," IAPB 12th World Congress and in Vitro Biology Meeting, 4 pages, Jun. 2010.
Cole et al., "The Jpred 3 secondary structure prediction server," Nucl Acids Res, 36:W197-W201, 2008.
Cornelis, "The type III secretion injectisome," Nat Rev Microbiol, 4:811-825, 2006.
Curtin et al., "Targeted mutagenesis of duplicated genes in soybean with zinc-finger nucleases," *Plant Physiology*, 156(2):466-473 (2011).
De Feyter et al., "Gene-for genes interactions between cotton R genes and Xanthomonas campestris pv. malvacearum avr genes," Mol Plant Microbe Interact, 6(2):225-237, 1993.
DeFrancesco, "Move over ZFNs," Nat Biotechnol, 29: 681-684, 2011.
Desjarlais and Berg, "Toward rules relating zinc finger protein sequences and DNA binding site preferences," Proc Natl Acad Sci USA, 89:7345-7349, 1992.
Domingues et al., "The Xanthomonas citri effector protein PthA interacts with citrus proteins involved in nuclear transport, protein folding and ubiquitination associated with DNA repair," Mol Plant Pathol, 11(5):663-675, DOI : 10.1111/ J .1364-3703.2010.00636.X, 13 pages, 2010.
Doyle et al., "TAL Effector-Nucleotide Targeter (TALE-NT) 2.0: tools for TAL effector design and target prediction," *Nucleic Acids Res*, 40:W117-122 (2012).
Draffehn et al., "Natural diversity of potato (*Solanum tuberosum*) invertases," *BMC Plant Biol.*, 2010, 10:271.
Durai et al., "Zinc finger nucleases: custom-designed molecular scissors for genome engineering of plant and mammalian cells," Nucl Acids Res, 33(1): 5978-5990, 2005.
Eisenschmidt et al., "Developing a programmed restriction endonuclease for highly specific DNA cleavage," Nucl Acids Res, 33:7039-7047, 2005.
Engler et al. "A One Pot, One Step, Precision Cloning Method with High Throughput Capability," PLoS One, 3: e3647, 7 pages, 2008.
Engler et al., "Golden Gate Shuffling: A One-Pot DNA Shuffling Method Based on Type IIs Restriction Enzymes," PLoS One, 4:e5553, 9 pages, 2009.
Fajardo-Sanchez et al., "Computer design of obligate heterodimer meganucleases allows efficient cutting of custom DNA sequences," Nucl Acids Res, 36(7):2163-2173, 2008.
Foley et al., "Rapid Mutation of Endogenous Zebrafish Genes Using Zinc Finger Nucleases Made by Oligomerized Pool ENgineering (OPEN)," PLoS One, 13 pages, 4:e4348, 2009.
Fonfara et al., "Creating highly specific nucleases by fusion of active restriction endonucleases and catalytically inactive homing endonucleases," Nucl Acids Res, 40(2):847-860, 2011.
Fujikawa et al., "Suppression of defense response in plants by the avrBs3/pthA gene family of *Xanthomonas* spp," Mol Plant Microbe Interact, 19(3):342-349, 2006.
Gabriel et al.," an unbiased genome-wide analysis of zinc-finger nuclease specificity," Nat Biotechnol, 29:816-823, 2011.
Geißler et al., "Transcriptional activators of human genes with programmable DNA-specificity," PLoS One, 6(5):e19509, May 2011.
GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.
GenBank Accession No. J04623, Apr. 26, 1993, 2 pages.
GenBank Accession No. M28828, Apr. 26, 1993, 3 pages.
GenBank Accession No. P14727, Jun. 28, 2011, 3 pages.
GenBank Accession No. X16130, Oct. 15, 2007, 3 pages.
Göhre and Robatzek, "Breaking the barriers: microbial effector molecules subvert plant immunity," Ann Rev Phytopathol, 46:189-215, 2008.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005,

(56) References Cited

OTHER PUBLICATIONS

Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
Gonzalez et al., "Molecular and pathotypic characterization of new *Xanthomonas oryzae* strains from West Africa," Mol Plant Microbe Interact, 20(5):534-546, 2007.
Govindarajulu et al., "Evaluation of constitutive viral promoters in transgenic soybean roots and nodules," *Mol. Plant Microbe Interact*, 21:1027-1035 (2008).
Greiner et al., "Ectopic expression of a tobacco invertase inhibitor homolog prevents cold-induced sweetening of potato tubers," *Nature Biotechnology*, 1999, 17(7):708-711.
Greisman and Pabo, "A general strategy for selecting high-affinity zinc finger proteins for diverse DNA target sites," Science, 275(5300):657-661, 1997.
Gu et al., "R gene expression induced by a type-III effector triggers disease resistance in rice," *Nature*, 2005, 435:1122-1125.
Gu et al., "Transcription activator-like type III effector AvrXa27 depends on OsTFIIAgamma5 for the activation of Xa27 transcription in rice that triggers disease resistance to *Xanthomonas oryzae* pv. oryzae," Mol Plant Pathol, 10(6):829-835, 2009.
Guan et al., "Heritable endogenous gene regulation in plants with designed polydactyl zinc finger transcription factors," Proc Natl Acad Sci USA, 99(20):13296-13301, 2002.
Gürlebeck et al., "Dimerization of the bacterial effector protein AvrBs3 in the plant cell cytoplasm prior to nuclear import," Plant J, 42:175-187, 2005.
Gürlebeck et al., "Type III effector proteins from the plant pathogen Xanthomonas and their role in the interaction with the host plant," J Plant Physiol, 163(3):233-255, 2006 (Epub 2005).
Gürlebeck et al., "Visualization of novel virulence activities of the Xanthomonas type III effectors AvrBsl, AvrBs3, and AvrBs4," Mol Plant Pathol, 10(2):175-188, 2009.
Haber, "In vivo biochemistry: Physical monitoring of recombination induced by site-specific endonucleases," Bioessays, 17:609-620, 1995.
Haberlach et al., "Isolation, culture and regeneration of protoplasts from potato and several related *Solanum* species," *Plant Science*, 1985, 39:67-74.
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem Soc Trans, 39:584-588, 2011.
Handel et al., "Expanding or restricting the target site repertoire of zinc-finger nucleases: the inter-domain linker as a major determinant of target site selectivity," Mol Ther, 17:104-111, 2009.
Haun et al., "Improved soybean oil quality by targeted mutagenesis of fatty acid desaturase 2 gene family," *Plant Biotechnology Journal*, 1-7 (2014).
Herbers et al., "Race-specificity of plant resistance to bacterial spot disease determined by repetitive motifs in a bacterial avirulence protein," Nature, 356:172-174, 1992.
Heuer et al., "Repeat domain diversity of avrBs3-like genes in Ralstonia solanacearum strains and association with host preferences in the field," Appl Environ Microbiol, 73(13):4379-4384, 2007.
Hockemeyer et al., "Genetic engineering of human pluripotent cells using TALE nucleases," Nat Biotechnol, 29(8):731-734, 2011.
Hopkins et al., "Identification of a family of avirulence genes from *Xanthomonas oryzae* pv. oryzae," Mol Plant Microbe Interact, 5(6):451-459, 1992.
Hu et al., "A virulence gene and insertion element-based RFLP as well as RAPD markers reveal high levels of genomic polymorphism in the rice pathogen *Xanthomonas oryzae* pv. oryzae," Syst Appl Microbiol, 30:587-600, 2007.
Huang et al., "Heritable gene targeting in zebrafish using customized TALENs," Nat Biotechnol, 29(8):699-700, 2011.
Hummel et al., "Rice gene activation by transcription activator-like effectors of *Xanthomonas oryzae* pvs. oryzae and oryzicola," poster presentation, and "A cipher-like mechanism governs TAL effector—DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc Natl Acad Sci USA, 100(21):12271-12276, 2003.
International Search Report and Written Opinion in International Application No. PCT/IB2013/003222, dated Aug. 18, 2014, 13 pages.
Isalan et al., "A rapid, generally applicable method to engineer zinc fingers illustrated by targeting the HIV-1 promoter," Nat Biotechnol, 19(7):656-660, 2001.
Jackel et al., "Protein design by directed devolution," Annu Rev Biophys, 37:155-173, 2008.
Jones and Dangl, "The plant immune system," Nature, 444:323-329, 2006.
Jordan et al., "Physical delimitation of the pepper Bs3 resistance gene specifying recognition of the AvrBs3 protein from Xanthomonas campestris pv. vesicatoria," Theor Appl Genet, 113(5):895-905, 2006.
Kay and Bonas, "How Xanthomonas type III effectors manipulate the host plant," Curr Opin Microbiol, 12:37-43, 2009.
Kay et al., "A bacterial effector acts as a plant transcription factor and induces a cell size regulator," *Science*, 2007, 318:648-651.
Kay et al., "Bacterial Effector Acts as a Plant Transcription Factor and Induces a Cell Size Regulator," Science, 318(5850):648-651, 2007.
Kay et al., "Characterization of AvrBs3-like effectors from a *Brassicaceae* pathogen reveals virulence and avirulence activities and a protein with a novel repeat architecture," Mol Plant Microbe Interact, 18(8):838-848, 2005.
Kay et al., "Detailed analysis of the DNA recognition motifs of the Xanthomonas type III effectors AvrBs3 and AvrBs3deltarep16," Plant J, 59(6):859-871, 2009.
Keshavarzi et al., "Basal defenses induced in pepper by lipopolysaccharides are suppressed by Xanthomonas campestris pv. vesicatoria," Mol Plant Microbe Interact, 17(7):805-815, 2004.
Kim and Chandrasegaran, "Chimeric restriction endonuclease," Proc Natl Acad Sci USA, 91(3):883-887 (Feb. 1994).
Kim et al., "Comparative analysis of three indigenous plasmids from Xanthomonas axonopodis pv. glycines," Plasmid, 56(2):79-87, 2006.
Kim et al., "Construction of a Z-DNA-specific restriction endonuclease," Proc Natl Acad Sci USA, 94(24):12875-12879, 1997.
Kim et al., "Hybrid restriction enzymes: zinc finger fusions to FokI cleavage," Proc Natl Acad Sci USA, 93:1156-1160, 1996.
Kim et al., "Site-specific cleavage of DNA—RNA hybrids by zinc finger/FokI cleavage domain fusions," Gene, 203(1):43-49, 1997.
Kim et al., "Targeted genome editing in human cells with zinc finger nucleases constructed via modular assembly," *Genome Res*, 19:1279-1288 (2009).
Knoop et al., "Expression of avirulence gene avrBs3 from Xanthomonas campestris pv. vesicatoria is not under the control of hrp genes and is independent of plant factors," J Bacteriol, 173(22):7142-7150, 1991.
Lahaye and Bonas, "Molecular secrets of bacterial type III effector proteins," Trends Plant Sci, 6(10):479-485, 2001.
Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.
Lee et al., "Environmental Effects on Oleic Acid in Soybean Seed Oil of Plant Introductions with Elevated Oleic Concentration," *Crop Science*, 49:1762-1768 (Sep./Oct. 2009).
Wu et al., "Developing Cold-chipping Potato Varieties by Silencing the Vacuolar Invertase Gene," Crop Science, 51(3):981-990 (May 2011).

(56) References Cited

OTHER PUBLICATIONS

Li et al., "Functional domains in FokI restriction endonuclease," Proc Natl Acad Sci USA, 89(10):4275-4279, 1992.
Li et al., "Modularly assembled designed TAL effector nucleases for targeted gene knockout and gene replacement in eukaryotes," Nucl Acids Res, 39:6315-6325, 2011.
Li et al., "TAL nucleases (TALNs): hybrid proteins composed of TAL effectors and FokI DNA-cleavage domain," Nucleic Acids Research, 39(1):359-372, 2010.
Liang et al., "Cloning and characterization of a novel avirulence gene (arp3) from *Xanthomonas oryzae* pv. oryzae," DNA Seq, 15(2):110-117, 2004.
Liu et al., "Design of polydactyl zinc-finger proteins for unique addressing within complex genomes," Proc Natl Acad Sci USA, 94(11):5525-5530, 1997.
Livak and Schmittgen, "Analysis of relative gene expression data using real-time quantitative PCR and the 2(-Delta C(T)) Method," *Method. Methods*, 2001, 25:402-408.
Mahfouz et al., "De novo-engineered transcription activator-like effector (TALE) hybrid nuclease with novel DNA binding specificity creates double-strand breaks," Proc Natl Acad Sci USA, 108:2623-2628, 2011.
Mahfouz et al., "TALE nucleases and next generation GM crops," *GM CROPS*, 2(2):99-103 (Apr. 2011).
MAK, "Sequence-specific DNA-binding TALEs," Nat Biotechnol, 29:43, 2011.
Marois et al., "The xanthomonas type III effector protein AvrBs3 modulates plant gene expression and induces cell hypertrophy in the susceptible host," Mol Plant Microbe Interact, 15(7):637-646, 2002.
Mercer et al., "Chimeric TALE recombinases with programmable DNA sequence specificity," Nucleic Acids Research, 40(21):11163-11172 (Nov. 2012).
Miller et al., "A TALE nuclease architecture for efficient genome editing," Nat Biotechnol, 29:143-148, 2011.
Miller et al., "An improved zinc-finger nuclease architecture for highly specific genome editing," Nature Biotechnol, 25:778-785, 2007.
Minczuk et al., "Development of a single-chain, quasi-dimeric zinc-finger nuclease for the selective degradation of mutated human mitochondrial DNA," Nucleic Acids Res, 36(12):3926-3938, 2008.
Mino et al., "Efficient double-stranded DNA cleavage by artificial zinc-finger nucleases composed of one zinc-finger protein and a single-chain FokI dimer," J Biotechnol, 140(3-4):156-161, 2009.
Moore et al., "Transactivated and chemically inducible gene expression in plants," Plant J, 45:651-683, 2006.
Morbitzer et al., "Assembly of custom TALE-type DNA binding domains by modular cloning," Nucleic Acids Research, 39(13):5790-5799, 2011.
Morbitzer et al., "Regulation of selected genome loci using de novo-engineered transcription activator-like effector (TALE)-type transcription factors," Proc Natl Acad Sci U S A., 107(50):21617-21622, 2010.
Moscou and Bogdanove, "A Simple Cipher Governs DNA Recognition by TAL Effectors," Science 326(5959): 1501, 2009.
Murakami et al., "The repeat domain of the type III effector protein PthA shows a TPR-like structure and undergoes conformational changes upon DNA interaction," Proteins, 78:3386-3395, 2010.
Murray et al., "Rapid isolation of high molecular weight plant DNA," *Nucl. Acids Res*, 8(19):4321-4325 (1980).
Mussolino et al., "A novel TALE nuclease scaffold enables high genome editing activity in combination with low toxicity," *Nucleic Acids Res.*, 2011, 39:9283-9293.
Nakagawa et al., "Development of series of gateway binary vectors, pGWBs, for realizing efficient construction of fusion genes for plant transformation," J Biosci Bioeng, 104:34-41, 2007.
Niño-Liu et al., "*Xanthomonas oryzae* pathovars: model pathogens of a model crop," Mol Plant Pathol, 7(5):303-324, 2006.

Nissan et al. "The type III effectors HsvG and HsvB of gall-forming Pantoea agglomerans determine host specificity and function as transcriptional activators." Molecular Microbiology, 61(5): 1118-1131, 2006.
Noël et al., "XopC and XopJ, two novel type III effector proteins from Xanthomonas campestris pv. vesicatoria," J Bacteriol, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," Curr Opin Plant Biol, 6:169-177, 2003.
Paques and Duchateau, "Meganucleases and DNA Double-Strand Break-Induced recombination: Perspectives for Gene Therapy," Curr Gene Ther, 7:49-66, 2007.
Park et al., "Avirulence gene diversity of Xanthomonas axonopodis pv. Glycines isolated in Korea," J Microbiol Biotechnol, 18(9):1500-1509, 2008.
Pattanayak et al., "Revealing off-target cleavage specificities of zinc-finger nucleases by in vitro selection," Nat Methods, 8:765-770, 2011.
Paulus et al., "Silencing β1,2-xylosyltransferase in transgenic tomato fruits reveals xylose as constitutive component in IgE-binding epitopes," *Frontiers in Plant Science*, 2(42), 12 pages (Aug. 2011).
Pavletich and Pabo, "Zinc finger-DNA recognition: crystal structure of a Zif268-DNA complex at 2.1 A," Science, 252:809-817, 1991.
Pearson, "The fate of fingers," Nature, 455:160-164, 2008.
Pennisi, "The Tale of the TALES," Science, 338(6113):1408-1411, 2012.
Pham et al., "Mutant alleles of FAD2-1A and FAD2-1B combine to produce soybeans with the high oleic acid seed oil trait," *BMC Plant Biol.*, 10:195 (2010).
Pingoud and Silva, "Precision genome surgery," Nature Biotechnol, 25(7):743-744, 2007.
Podhajska and Szybalski, "Conversion of the FokI endonuclease to a universal restriction enzyme: cleavage of phage M13mp7 DNA at predetermined sites," Gene, 40(2-3):175-182, 1985.
Pomerantz et al., "Structure-based design of transcription factors," Science, 267(5194):93-96, 1995.
Porteus and Baltimore, "Chimeric nucleases stimulate gene targeting in human cells," Science, 300:763, 2003.
Porteus and Carroll, "Gene targeting using zinc finger nucleases," Nature Biotechnol, 23:967-973, 2005.
Porteus, "Zinc fingers on target," Nature, 459: 337-338, 2009.
Potenza et al., "Targeting transgene expression in research, agricultural, and environmental applications: Promoters used in plant transformation," In vitro Cell Dev Biol, 40(1):1-22, 2004.
Puchta et al., "Homologous recombination in plant cells is enhanced by in vivo induction of double strand breaks into DNA by a site-specific endonuclease," Nucl Acids Res, 21(22):5034-5040, 1993.
Radecke et al., "Zinc-finger nuclease-induced gene repair with oligodeoxynucleotides: wanted and unwanted target locus modifications," Mol Ther, 18(4):743-753, 2010.
Reyon et al., "FLASH assembly of TALENs for high-throughput genome editing," *Nat. Biotechnol.*, 2012, 30:460-465.
Römer et al., "A single plant resistance gene promoter engineered to recognize multiple TAL effectors from disparate pathogens," Proc Natl Acad Sci USA, 106(48):20526-31, 2009.
Romer et al., "Plant pathogen recognition mediated by promoter activation of the pepper Bs3 resistance gene," *Science*, 2007, 318:645-648.
Römer et al., "Promoter elements of rice susceptibility genes are bound and activated by specific TAL effectors from the bacterial blight pathogen, *Xanthomonas oryzae* pv. oryzae," New Phytol, 187:1048-1057, 2010.
Römer et al., "Recognition of AvrBs3-Like Proteins Is Mediated by Specific Binding to Promoters of Matching Pepper Bs3 Alleles," Plant Physiol, 150:1697-1712, 2009.
Romero et al., "Temperature Sensitivity of the Hypersensitive Response of Bell Pepper to Xanthomonas axonopodis pv. vesicatoria," Phytopathology, 92(2):197-203, 2002.

(56) References Cited

OTHER PUBLICATIONS

Rossier et al., "HrpB2 and HrpF from Xanthomonas are type III-secreted proteins and essential for pathogenicity and recognition by the host plant," Mol Microbiol, 38(4):828-838, 2000.
Rossier et al., "The Xanthomonas Hrp type III system secretes proteins from plant and mammalian bacterial pathogens," Proc Natl Acad Sci USA, 96(16):9368-9373, 1999.
Rouet et al., "Expression of a site-specific endonuclease stimulates homologous recombination in mammalian cells," Proc Natl Acad Sci USA, 91(13):6064-6068, 1994.
Rouet et al., "Introduction of double-strand breaks into the genome of mouse cells by expression of a rare-cutting endonuclease," Mol Cell Biol, 14(12):8096-8106, 1994.
Rybak et al., "Identification of Xanthomonas citri ssp. citri host specificity genes in a heterologous expression host," Mol Plant Pathol, 10(2):249-262, 2009.
Sandhu et al., "Enhanced oleic acid content in the soybean mutant M23 is associated with the deletion in the Fad2-1a gene encoding a fatty acid desaturase," *JAOCS*, 84:229-235 (2007).
Santiago et al., "Targeted gene knockout in mammalian cells by using engineered zinc-finger nucleases," Proc Natl Acad Sci USA, 105(15):5809-5814, 2008.
Scholze and Boch, "TAL effectors are remote controls for gene activation," Curr Opin Microbiol, 14:47-53, 2011.
Scholze and Boch. "TAL effector-DNA specificity," Virulence, 1(5):428-432, 2010.
Schornack et al., "Characterization of AvrHah1, a novel AvrBs3-like effector from Xanthomonas gardneri with virulence and avirulence activity," New Phytol, 179:546-556, 2008.
Schornack et al., "Expression levels of avrBs3-like genes affect recognition specificity in tomato Bs4-but not in pepper BS3-mediated perception," Mol Plant-Microbe Interact, 18(11):1215-1225, 2005.
Schornack et al., "Gene-for-gene-mediated recognition of nuclear-targeted AvrBs3-like bacterial effector proteins," *J Plant Physiol*, 2006, 163:256-272.
Schornack et al., "The tomato resistance protein Bs4 is a predicted non-nuclear TIR-NB-LRR protein that mediates defense responses to severely truncated derivatives of AvrBs4 and overexpressed AvrBs3," Plant J, 37(1):46-60, 2004.
Segal et al., "Endonuclease-induced, targeted homologous extrachromosomal recombination in Xenopus oocytes," Proc Natl Acad Sci USA, 92(3):806-810, 1995.
Sera, "Inhibition of virus DNA replication by artificial zinc finger proteins," J Virol, 79(4):2614-2619, 2005.
Shepard and Totten, "Mesophyll cell protoplasts of potato: isolation, proliferation, and plant regeneration," *Plant Physiol*., 1977, 60:313-316.
Shukla et al., "Precise genome modification in the crop species *Zea mays* using zinc-finger nucleases," Nature, 459(7245):437-441, 2009.
Simon et al., "Targeting DNA with triplex-forming oligonucleotides to modify gene sequence," Biochimie, 90:1109-1116, 2008.
Skipper, "Technology: The holy grail for plant biologists," Nature Reviews Genetics, 10(6):350, 2009.
Strasser et al., "Generation of glycol-engineered *Nicotiana bethamiana* for the production of monoclonal antibodies with a homogeneous human-like N-glycan structure," *Plant Biotechnology Journal*, 6:392-402 (2008).
Studholme et al., "Genome-wide sequencing data reveals virulence factors implicated in banana Xanthomonas wilt," FEMS Microbiol Left., 310(2):182-192, 2010.
Sugio et al., "Two type III effector genes of *Xanthomonas oryzae* pv. oryzae control the induction of the host genes OsTFXIAgammal and OsTFX1 during bacterial blight of rice," *Proc. Natl. Acad. Sci. USA*, 2007, 104:10720-10725.
Swarup et al., "An Xanthomonas citri pathogenicity gene, pthA, pleiotropically encodes gratuitous avirulence on nonhosts," Mol Plant Microbe Interact, 5(3):204-213, 1992.
Szurek et al. "Type III-dependent translocation of the Xanthomonas AvrBs3 protein into the plant cell," Mol Microbiol, 46(1): 13-23, 2002.
Szurek et al., "Eukaryotic features of the Xanthomonas type III effector AvrBs3: protein domains involved in transcriptional activation and the interaction with nuclear import receptors from pepper," Plant J, 26(5):523-534, 2001.
Takenaka et al., "Inhibition of tomato yellow leaf curl virus replication by artificial zinc-finger proteins," Nucl Acids Symposium Series, 51(1):429-430, 2007.
Thieme et al., "New type III effectors from Xanthomonas campestris pv. vesicatoria trigger plant reactions dependent on a conserved N-myristoylation motif," Mol Plant Microbe Interact, 20(10):1250-1261, 2007.
Thierry et al., "Cleavage of yeast and bacteriophage T7 genomes at a single site using the rare cutter endonuclease I-Sce I," Nucl Acids Res, 19(1):189-190, 1991.
Tovkach et al., "A toolbox and procedural notes for characterizing novel zinc finger nucleases for genome editing in plant cells," Plant J, 57:747-757, 2009.
Townsend et al., "High-frequency modification of plant genes using engineered zinc-finger nucleases," Nature, 459:442-445, 2009.
Urnov et al., "Highly efficient endogenous human gene correction using designed zinc-finger nuclease," Nature, 435(7042):646-651, 2005.
Van Den Ackerveken et al., "Recognition of the bacterial avirulence protein AvrBs3 occurs the host plant cell," Cell, 87(7):1307-1316, 1996.
Van Den Elzen et al., "A chimaeric hygromycin resistance gene as a selectable marker in plant cells," *Plant Molecular Biology*, 5:299-302 (1985).
Vergunst et al., "VirB/D4-Dependent Protein Translocation from Agrobacterium into Plant Cells," Science, 290:979-982, 2000.
Voytas et al., "DNA binding made easy," Science, 326(5959):1491-1492, 2009.
Wah et al., "Structure of FokI has implications for DNA cleavage," Proc Natl Acad Sci USA, 95(18):10564-10569, 1998.
Wah et al., "Structure of the multimodular endonuclease FokI bound to DNA," Nature, 388(3):97-100, 1997.
Wang et al., "Chemically regulated expression systems and their applications in transgenic plants," Transgenic Res, 12:529-540, 2003.
Weber et al., "The type III-dependent Hrp pilus is required for productive interaction of Xanthomonas campestris pv. vesicatoria with pepper host plants," J Bacteriol, 187(7):2458-2468, 2005.
White and Yang, "Host and pathogen factors controlling the rice/*Xanthomonas oryzae* interaction," Plant Physiol, 150:1677-1686, 2009.
White et al., "The type III effectors of Xanthomonas," Mol Plant Pathol, 10:749-766, 2009.
Wright et al., "High-frequency homologous recombination in plants mediated by zinc-finger nucleases," *Plant J*, 44:693-705 (2005).
Yang and White, "Diverse members of the AvrBs3/PthA family of type III effectors are major virulence determinants in bacterial blight disease of rice," Mol Plant Microbe Interact, 17(11):1192-1200, 2004.
Yang et al. "The virulence factor AvrXa7 of *Xanthomonas oryzae* of Oryzae is a type III secretion pathway-dependent nuclear-localized double stranded DNA binding protein," Proc Natl Acad Sci USA, 97(17): 9807-9812, 2000.
Yang et al., "Avoidance of host recognition by alterations in the repetitive and C-terminal regions of AvrXa7, a type III effector of *Xanthomonas oryzae* pv. oryzae," Mol Plant Microbe Interact, 18(2):142-149, 2005.
Yang et al., "Os8N3 is a host disease-susceptibility gene for bacterial blight of rice," *Proc. Natl. Acad. Sci USA*, 2006, 103:10503-10508.
Y00 et al., "Arabidopsis mesophyll protoplasts: a versatile cell system for transient gene expression analysis," *Nature Protocols*, 2007, 2:1565-1572.
Yuan et al., "Characterization of *Xanthomonas oryzae*—responsive cis-acting element in the promoter of rice race-specific susceptibility gene Xa13," Mol Plant, 4(2):300-309, 2011.

(56) References Cited

OTHER PUBLICATIONS

Zhang et al., "Efficient construction of sequence-specific TAL effectors for modulating mammalian transcription," *Nat. Biotechnol.*, 2011, 29:149-153.
Zhang et al., "High frequency targeted mutagenesis in *Arabidopsis thaliana* using zinc finger nucleases," *Proc Natl Acad Sci USA*, 107(26):12028-12033 (2010).
Zhang et al., "RNAi effects on regulation of endogenous acid invertase activity in potato (*Solanum tuberosum* L.) tubers," *Chin J Agric. Biotechnol*, 2008, 5:107-111.
Zhang et al., "Transcription Activator-Like Effector Nucleases Enable Efficient Plant Genome Engineering," Plant Physiology, 161(1):20-27 (Nov. 2012).
Zhu et al., "The C terminus of AvrXa10 can be replaced by the transcriptional activation domain of VP16 from the herpes simplex virus," Plant Cell, 11(9):1665-1674, 1999.
Zhu et al., "AvrXa10 Contains an Acidic Transcriptional Activation Domain in the Functionally Conserved C Terminus," Molecular Plant-Microbe Interactions, 11(8): 824-832, 1998.
Zhu et al., "The rsma-like gene rsmA(XOO) of *Xanthomonas oryzae* pv. oryzae regulates bacterial virulence and production of diffusible signal factor," Mol Plant Pathol, 12(3):227-237, 2011, Epub 2010.
Zou et al., "Identification of an avirulence gene, avrxa5, from the rice pathogen *Xanthomonas oryzae* pv. oryzae," Sci China Life Sci, 53(12):1440-1449, 2010.
Zrenner et al., "Soluble acid invertase determines the hexos-to sucrose ratio in cold-stored potato tubers," *Planta*, 1996, 198(2):246-252.
Zuo and Chua, "Chemical-inducible systems for regulated expression of plant genes," Curr Opin Biotechnol, 11:146-151, 2000.
Zuo et al., "Technical advance: An estrogen receptor-based transactivator XVE mediates highly inducible gene expression in transgenic plants," *Plant J.* 24:265-273 (2000).
Draffehn et al., 2010, BMC Plant. Bio., 10: 1-15.
Huang, "Molecular analysis of an acid invertase gene family in *Arabidopsis*," Doctoral dissertation, University of Florida, 2006.

Klann et al., "Expression of acid invertase gene controls sugar composition in tomato (Lycopersicon) fruit," Plant. Physiol., 103: 863-870, 1993.
Mitsuhashi et al., "Differential expression of acid invertase genes during seed germination in *Arabidopsis thaliana*," Biosci. Biotechnol. Biochem., 68: 602-608, 2004.
Ou et al., "Promoter regions of potato vacuolar invertase gene in response to sugars and hormones," Plant Phys. Biochem., 69: 9-16, 2013 (published online Apr. 30, 2015).
Sebkova et al., "Biochemical, physiological and molecular characterization of sucrose synthase from Daucus carota," Plant Physiol, 108: 75-83, 1995.
Tang et al., "Antisense repression of vacuolar and cell wall invertase in transgenic carrot alters early plant development and sucrose partitioning," Plant Cell, 11: 177-189, 1999.
Chinese Office Action in Chinese Application No. 201380071363.8, dated Aug. 2, 2016, 14 pages (English Translation).
Clasen et al., "Improving cold storage and processing traits in potato through targeted gene knockout" *Plant Biotech J.*, 14(1):169-176, 2016 (published online Apr. 7, 2015); includes supplemental figures retrieved from http://onlinelibrary.wiley.com/doi/10.1111/pbi.12370/full.
European Communication Pursuant to Article 94(3) EPC in European Application No. 13861523.2, dated Feb. 3, 2017, 6 pages.
Lusser et al., "Deployment of New Biotechnologies in Plant Breeding," *Nature Biotechnology.*, 30(3):231-239, Mar. 2012.
Rossi et al., "Genetic compensation induced by deleterious mutations but not gene knockdowns," *Nature.*, 524(7564):230-233, Aug. 2015.
Waltz., "Tiptoeing around Transgenics," *Nature Biotechnology.*, 30(3):215-217, Mar. 2012.
Chinese Office Action in Chinese Application No. 201380071363.8, dated Jun. 9, 2017, 6 pages (English Translation).
Chinese Office Action in Chinese Application No. 201380071363.8, dated Jan. 26, 2018, 15 pages (with English Translation).
U.S. Appl. No. 15/334,017, filed Oct. 25, 2016, Mathis et al.

\* cited by examiner

Figure 1

VInv_T1
AttcctcccggatcaaccCgattccggccaccggaagtcccttaaaatcatctccggcatttcctctcctcttcct
tttgctttctgtagccttctttccgatcctcaacaaccaGtcaccgacttgcagagtaac (SEQ ID NO:1)

VInv_T2
AttcctcccggatcaaccCgattccggccaccggaagtcccttaaaatcatctccggcatttcctctcctcttcct
tttgctttctgtagccttctttccgatcctcaacaaccaGtcaccgacttgcagagtaac (SEQ ID NO:1)

VInv_T3
AttcctcccggatcaaccCgattccggccaccggaagtcccttaaaatcatctccggcatttcctctcctcttcct
tttgctttctgtagccttctttccgatcctcaacaaccaGtcaccgacttgcagagtaac (SEQ ID NO:1)

Figure 2

VInv_T1

| Sequence | Number of Deletions | SEQ ID NO: |
|---|---|---|
| TTCCTCCCGGATCAACCCGATTCCGGCCACCGGAAGTCCCTTAAAATCA | 0 | 2 |
| TTCCTCCCGGATCAACTCCCTT----------------------AAATCA | 21 | 3 |
| TTCCTCCCGGATCAGCCACCGGAAATC----------CCTTAAAACTCA | 10 | 4 |
| TTCCTCCCGGATCAACCCGATT-------------GTCCCTTAAAATCA | 13 | 5 |
| TTCCTCCCGGATCAACCCGAT----------------------------- | 38 | 6 |
| TTCCTCCCGGATCAACCCGATTCCGGC---------------------- | 30 | 7 |

VInv_T2

| Sequence | Number of Deletions | SEQ ID NO: |
|---|---|---|
| TTCCTCCTCCTTTCCTTTGCTTTCTGTAGCCTTCTTTCCGATCCTCA | 0 | 8 |
| TTCCTCCTCCTTTCCTTTTGCT------AGCCTTCTTTCCGATCCTCA | 6 | 9 |
| TTCCTCCTCCTTTCCTTTGCTTT---TAGTCTTCTTTCCGATCCTCA | 3 | 10 |
| TTCCTCCTCCTTTCCTTTTGCTGT----AGCCTTCTTTCCGATCCTCA | 4 | 11 |
| TTCCTCCTCCTTTCCTTTTGCT------AGCCTTCTTTCCGATCCTCA | 6 | 9 |
| TTCCTCCTCCTTTCCTTTTGCGT-----AGCCTTCTTTCCGATCCTCA | 5 | 12 |

VInv_T3

| Sequence | Number of Deletions | SEQ ID NO: |
|---|---|---|
| TAGCCTTCTTTCCGATCCTCAACAACCAGTCACCGGACTTGCAGAGTAA | 0 | 13 |
| TAGCCTTCTTTCCGATCCTCAAC------ACACCGGACTTGCAGAGTAA | 6 | 14 |
| TAGCCTTCTTTCCGATCCTCAAA-----GTCACCGGACTTGCAGAGTAA | 5 | 15 |
| TAGCCTTCTTTCCGATCCTC---------TCACCGGACTTGCAGAGTAA | 9 | 16 |
| TAGCCTTCTTTCCGATCCTCAG-------TCACCGGACTTGCAGAGTAA | 7 | 17 |
| TAGCCTTCTTTCCGATCCTCAG-------TCACCGGACTTGCAGAGTAA | 7 | 17 |

Figure 3

```
VInv_T2 Alleles 1-3 (A1-A3)

10         20         30         40         50         60         70         80         90
              |          |          |          |          |          |          |          |          |
    1 ATAGCTCTCGCAGTTATGACCCGGAAACTCCGCCTCCCCATTACACATTCCTCCCGGATCAACCTGATTCCGGCCACCGGAAGTCCCTTAA
    1 ATAGCTCTCGCAGTTATGACCCGGAAACTCCGCCTCCCCATTACACATTCCTCCCGGATCAACCCGATTCCGGCCACCGGAAGTCCCTTAA
    1 ATAGCTCTCGCAGTTATGACCCGGAAACTCCGCCTCCCCATTACACATTCCTCCCGGATCAACACGATTCCGGCCACCGGAAATCCCTTAA 100        110        120        130        140        150        160        170        180
              |          |          |          |          |          |          |          |          |
   91 AATCATCTCCGGCATTTCCTCTCCTCTTTGCTTTCCTTTCTGTAGCCTTCTTTCCGATCCTCAACAACCAGTCACCGGACTTGCAGAG
   91 AATCATCTCCGGCATTTCCTCTCCTCTTTGCTTTCCTTTCTGTAGCCTTCTTTCCGATCCTCAACAACCAGTCACCGGACTTGCAGAG
   91 AATCATCTCCGGCATTTCCTCTCCTCTCCTTTTCTTTGCTTTCTTATCCTTCTTTCCGATCCTCAACAACCAGTCACCGGACTTGAAAAG 190        200        210        220        230
              |          |          |          |          |
  181 TAACTCCCGTTCGCCGGCCGCCGCCGTCAAGAGGTGTTTCTCAGGGAGTCT A3 (SEQ ID NO:28)
  181 TAACTCCCGTTCGCCGGCCGCCGCCGTCAAGAGGTGTTTCTCAGGGAGTCT A2 (SEQ ID NO:29)
  181 TAACGCCCGTTCGCCGGCCGCCGCCGTCAAGAGGTGTTTCTCAGGGAGTCT A1 (SEQ ID NO:30)
```

Figure 4

| VInv_T2 Site | Number of Deletions | SEQ ID NO: |
|---|---|---|
| TTCCTCTCCTCTCTCCTTTGCTTTCTTTAGTCTTCTTTCCGATCCTCA | 0 | 31 |
| TTCCTCTCCCTCTTCCTTTGCT----GTAGCCTTCTTTCCGATCCTCA | 4 | 32 |
| TTCCTCTCCCTCTCCCTTTTGCTT---TAGTCTTCTTTCCGATCCTCA | 4 | 33 |
| TTCCTCTCCCTCT-----------------AGCCTTCTTTCCGATCCTCA | 17 | 34 |

POTATOES WITH REDUCED COLD-INDUCED SWEETENING

CROSS-REFERENCE TO RELATED APPLICATIONS

This application is a National Stage application under 35 U.S.C. § 371 of International Application No. PCT/IB2013/003222, having an International Filing Date of December 20, 2013, which claims priority from U.S. Provisional Application Ser. No. 61/745,003, filed December 21, 2012. The disclosure of the prior applications are considered part of (and are incorporated by reference in) the disclosure of this application.

TECHNICAL FIELD

This document provides materials and methods for creating potato varieties with reduced cold-induced sweetening.

BACKGROUND

Potato (*Solanum tuberosum*) is an important food crop, with worldwide production estimated at 324 million metric tons in 2011 (Food and Agricultural Organization of the United Nations (FAOSTAT), 2010 Crop Production Data, online at faostat.fao.org/site/567/DesktopDefault.aspx?PageID=567#ancor). A large proportion of the total potato crop (61% of the 2010 crop in the United States) is used by processors to produce potato chips, French fries and other processed products. In order to have a year-round supply of high-quality raw potatoes for the processing industry, it is necessary to 'cold-store' the potato tubers until they are needed. Cold storage is variety/processor specific, with temperatures ranging from 3° C. to 13° C. for up to twelve months, which prevents sprouting, reduces losses due to shrinkage/aging, and minimizes the spread of disease.

SUMMARY

This document provides materials and methods for creating potato varieties that have reduced cold-induced sweetening (CIS), which is a phenomenon by which starch is converted to the simple reducing sugars, glucose and fructose, during cold storage. Upon processing at high temperatures, the glucose/fructose can interact with free amino acids in a Maillard reaction, which results in bitter, dark-pigmented products that may have increased levels of acrylamide—a suspected neurotoxin/carcinogen. Potato varieties with reduced CIS also are provided.

The disclosure herein is based at least in part on the discovery that potatoes having reduced CIS can be obtained by using a sequence-specific nuclease to make a targeted mutation or knockout in the vacuolar invertase (VInv) gene. The modified potatoes can have improved storage characteristics and reduced levels of acrylamide upon frying, as compared to the levels of acrylamide in non-modified potatoes upon frying after cold storage. Further, the potatoes do not carry any foreign DNA and therefore may be considered by regulatory agencies as non-GM. This document also is based at least in part on the development of potato cultivars with loss-of-function VInv mutations that are created by sequence-specific nucleases.

In one aspect, this document features a *Solanum* plant, plant part, or plant cell comprising a mutation in at least two VInv alleles endogenous to the plant, plant part, or plant cell, such that the plant, plant part, or plant cell has reduced expression of vacuolar invertase as compared to a control *Solanum* plant, plant part, or plant cell that lacks the mutation. Each mutation can be a deletion of more than one nucleotide base pair. Each mutation can be at a target sequence as set forth in SEQ ID NO:27, or a target sequence having at least 95 percent identity to SEQ ID NO:27; or at a target sequence as set forth in SEQ ID NO:1, or a target sequence having at least 95 percent identity to SEQ ID NO:1. The plant, plant part, or plant cell can have been made using a rare-cutting endonuclease [e.g., a transcription activator-like effector endonuclease (TALE-nuclease)]. The TALE-nuclease can bind to a sequence as set forth in any of SEQ ID NOS:18-23. Each of the at two least VInv alleles can exhibit removal of an endogenous nucleic acid and does not include any exogenous nucleic acid. Every endogenous VInv allele can be mutated. Each VInv allele can exhibit removal of an endogenous nucleic acid, without including any exogenous nucleic acid. The plant, plant part, or plant cell may have no detectable expression of vacuolar invertase. The *Solanum* plant, plant part, or plant cell can be a *S. tuberosum* plant, plant part, or plant cell. The plant, plant part, or plant cell can be subjected to cold storage conditions. The plant, plant part, or plant cell can have decreased levels of acrylamide as compared to a control plant, plant part, or plant cell that lacks the mutation.

In another aspect, this document features a method for making a *Solanum* plant that has reduced cold-induced sweetening. The method can include (a) contacting a population of *Solanum* plant cells containing a functional VInv allele with a rare-cutting endonuclease targeted to an endogenous VInv sequence, (b) selecting, from the population, a cell in which at least two VInv alleles have been inactivated, and (c) growing the selected plant cell into a *Solanum* plant, wherein the *Solanum* plant has reduced cold-induced sweetening as compared to a control *Solanum* plant in which the VInv alleles have not been inactivated. The *Solanum* plant cells can be protoplasts. The method can include transforming the protoplasts with a nucleic acid encoding the rare-cutting endonuclease. The nucleic acid can be an mRNA. The nucleic acid can be contained within a vector. The method can include introducing into the protoplasts a rare-cutting endonuclease protein. The rare-cutting endonuclease can be a TALE-nuclease. The TALE-nuclease can be targeted to a sequence as set forth in SEQ ID NO:27 or to a sequence having at least 95 percent identity to the sequence set forth in SEQ ID NO:27, or can be targeted to a sequence as set forth in SEQ ID NO:1 or to a sequence having at least 95 percent identity to the sequence set forth in SEQ ID NO:1. The TALE-nuclease can bind to a sequence as set forth in any of SEQ ID NOS:18-23. The method can further include culturing protoplasts to generate plant lines. The method can include isolating genomic DNA containing at least a portion of the VInv locus from the protoplasts. The *Solanum* plant cells can be *S. tuberosum* plant cells.

In another aspect, this document features a method for producing a food product. The method can include (a) providing a *Solanum* plant or plant part that (i) contains a mutation in at least two VInv alleles endogenous to the plant or plant part, such that the plant, plant part, or plant cell has reduced expression of vacuolar invertase as compared to a control *Solanum* plant or plant part that lacks the mutation, and (ii) has been subjected to cold storage; and (b) producing a food product from the plant or plant part. The method can further include (c) cooking the plant or plant part to obtain a food product having reduced levels of acrylamide as compared to a food product produced from a control cooked plant or plant part that lacks the mutation and that was subjected to cold-induced storage prior to being cooked. The cooked plant or plant part can have about the same level of acrylamide as a cooked *Solanum* plant or plant part that was not subjected to cold storage prior to cooking. Each mutation can be at a target sequence as set forth in SEQ ID NO:27 or a target sequence having at least 95 percent identity to SEQ ID NO:27, or at a target sequence as set forth in SEQ ID NO:1 or a target sequence having at least 95 percent identity to SEQ ID NO:1. Each mutation can have been made using a rare-cutting endonuclease (e.g., a TALE-nuclease). The TALE-nuclease can bind to a sequence as set forth in any of SEQ ID NOS:18-23. The *Solanum* plant or plant part can be a *S. tuberosum* plant or plant part. The *Solanum* plant or plant part may have no detectable expression of vacuolar invertase.

In still another aspect, this document features a food product produced from a *Solanum* plant or plant part that (i) contains a mutation in each VInv allele endogenous to the plant or plant part, such that the plant, plant part, or plant cell has no functional VInv allele, and (ii) has been subjected to cold storage. Each mutation can be at a target sequence as set forth in SEQ ID NO:27 or a target sequence having at least 95 percent identity to SEQ ID NO:27, or at a target sequence as set forth in SEQ ID NO:1 or a target sequence having at least 95 percent identity to SEQ ID NO:1. Each mutation can have been made using a rare-cutting endonuclease (e.g., a TALE-nuclease). The TALE-nuclease can bind to a sequence as set forth in any of SEQ ID NOS:18-23. The food product can have been cooked. The food product can have decreased levels of acrylamide as compared to a cooked food product made from a control plant or plant part that lacks the mutation and that was subjected to cold storage prior to being cooked. The cooked food product can have about the same level of acrylamide as a *Solanum* plant or plant part that has not been subjected to cold storage. The *Solanum* plant or plant part can be a *S. tuberosum* plant or plant part (e.g., from a variety selected from the group consisting of Ranger Russet, Atlantic, and Burbank). The food product can be a potato chip or a French fry.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows target sites for VInv TALE-nucleases. A DNA sequence from the VInv gene is shown (SEQ ID NO:1). The underlined sequences represent target sites (SEQ ID NOS:18-23) for TALE-nucleases that recognize the VInv gene.

FIG. 2 shows examples of TALE-nuclease-induced mutations in the VInv gene. The top line of each panel shows the DNA sequence of the recognition site for the VInv TALE-nucleases (underlined). The other sequences show representative mutations that were induced by imprecise non-homologous end joining (NHEJ). Deletion sizes are given on the right.

FIG. 3 shows exemplary alleles of the VInv 2 locus for the variety "Ranger Russet," which was the germplasm used for development of a mutant plant. Diagnostic single nucleotide polymorphisms (SNPs) that differentiate allele types are underlined and in bold type.

FIG. 4 shows exemplary deletion profiles for a regenerated mutant "Ranger Russet" plant. TALE nuclease recognition sites are underlined, and SNP sites are shaded.

DETAILED DESCRIPTION

The potato genome contains a small family of enzymes called invertases, which play an important role in regulating the carbon partitioning between source tissues (leaves) and sink tissues (tubers, fruits, seeds). The enzymes irreversibly catalyze the starch→sucrose→glucose/fructose reaction. Plants have three classes of invertase enzymes, but the vacuolar invertase (VInv) is thought to play an important role in CIS.

This document provides potato plant varieties, particularly of the species *S. tuberosum*, that have reduced or even lack VInv activity. Methods for generating such plant varieties, methods for using such plant varieties to produce food products, and food products produced from such plant varieties also are provided.

As used herein, the terms "plant" and "plant part" refer to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

The term "allele(s)" means any of one or more alternative forms of a gene at a particular locus. In a diploid (or amphidiploid) cell of an organism, alleles of a given gene are located at a specific location or locus on a chromosome, with one allele being present on each chromosome of the pair of homologous chromosomes. Similarly, in a tetraploid cell of an organism, one allele is present on each chromosome of the group of four homologous chromosomes. "Heterozygous" alleles are different alleles residing at a specific locus, positioned individually on corresponding homologous chromosomes. "Homozygous" alleles are identical alleles residing at a specific locus, positioned individually on corresponding homologous chromosomes in the cell.

"Wild type" as used herein refers to a typical form of a plant or a gene as it most commonly occurs in nature. A "wild type VInv allele" is a naturally occurring VInv allele (e.g., as found within naturally occurring *S. tuberosum* plants) that encodes a functional VInv protein, while a "non-functional mutant VInv allele" is a VInv allele that does not encode a functional VInv protein. Such a "non-functional mutant VInv allele" can include one or more mutations in its nucleic acid sequence, where the mutation(s) result in no detectable amount of functional VInv protein in the plant or plant cell in vivo.

The potato genome usually contains only one VInv gene, but because cultivated potato is a tetraploid, multiple alleles of VInv are present in each variety. The methods provided herein can be used to inactivate at least one (e.g., at least two, at least three, or all four) functional alleles of VInv, thereby removing at least some full-length RNA transcripts and functional VInv protein from potato cells, and in some cases completely removing all full-length RNA transcripts and functional VInv protein.

A representative example of a naturally occurring *S. tuberosum* VInv nucleotide sequence is shown in Table 4 herein. The *S. tuberosum* plants, cells, plant parts, seeds, and progeny thereof that are provided herein have a mutation in each endogenous VInv allele, such that expression of the gene is reduced or completely inhibited. Thus, in some cases, the plants, cells, plant parts, seeds, and progeny do not exhibit detectable levels of vacuolar invertase expressed from the VInv gene.

The plants, plant cells, plant parts, seeds, and progeny provided herein can be generated using a TALE-nuclease system to make a targeted knockout in each allele of the VInv gene. Thus, this document provides materials and methods for using rare-cutting endonucleases (e.g., TALE-nucleases) to generate potato plants and related products (e.g., seeds and plant parts) that are particularly suitable for cold storage before use in making food products for human and animal consumption, due to targeted knockouts in the VInv gene. Other sequence-specific nucleases also may be used to generate the desired plant material, including engineered homing endonucleases or zinc finger nucleases.

The term "rare-cutting endonucleases" herein refer to natural or engineered proteins having endonuclease activity directed to nucleic acid sequences having a recognition sequence (target sequence) about 12-40 bp in length (e.g., 14-40, 15-36, or 16-32 bp in length). Typical rare-cutting endonucleases cause cleavage inside their recognition site, leaving 4 nt staggered cuts with 3'OH or 5'OH overhangs. These rare-cutting endonucleases may be meganucleases, such as wild type or variant proteins of homing endonucleases, more particularly belonging to the dodecapeptide family (LAGLIDADG (SEQ ID NO:28); see, WO 2004/067736) or may result from fusion proteins that associate a DNA binding domain and a catalytic domain with cleavage activity. TAL-effector endonucleases (TALE-nucleases) and zinc-finger-nucleases (ZFN) are examples of fusions of DNA binding domains with the catalytic domain of the endonuclease FokI. Customized TALE-nucleases are commercially available under the trade name TALEN™ (Cellectis, Paris, France). For a review of rare-cutting endonucleases, see Baker, *Nature Methods* 9:23-26, 2012).

"Mutagenesis" as used herein refers to processes in which mutations are introduced into a selected DNA sequence. Mutations induced by endonucleases generally are obtained by a double strand break, which results in insertion/deletion mutations ("indels") that can be detected by deep-sequencing analysis. Such mutations typically are deletions of several base pairs, and have the effect of inactivating the mutated allele. In the methods described herein, for example, mutagenesis occurs via double stranded DNA breaks made by TALE-nucleases targeted to selected DNA sequences in a plant cell. Such mutagenesis results in "TALE-nuclease-induced mutations" (e.g., TALE-nuclease-induced knockouts) and reduced expression of the targeted gene. Following mutagenesis, plants can be regenerated from the treated cells using known techniques (e.g., planting seeds in accordance with conventional growing procedures, followed by self-pollination).

The term "expression" as used herein refers to the transcription of a particular nucleic acid sequence to produce sense or antisense RNA or mRNA, and/or the translation of an mRNA molecule to produce a polypeptide (e.g., a therapeutic protein), with or without subsequent post-translational events.

"Reducing the expression" of a gene or polypeptide in a plant or a plant cell includes inhibiting, interrupting, knocking-out, or knocking-down the gene or polypeptide, such that transcription of the gene and/or translation of the encoded polypeptide is reduced as compared to a corresponding control plant or plant cell in which expression of the gene or polypeptide is not inhibited, interrupted, knocked-out, or knocked-down. Expression levels can be measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

In general, a *Solanum* plant, plant part, or plant cell can have its expression of vacuolar invertase reduced by more than 60 percent (e.g., by more than 70 percent, more than 80 percent, or more than 90 percent) as compared to a control *Solanum* plant that lacks the mutation(s). The control *Solanum* plant can be, for example, the wild-type of the *Solanum* plant of which the invertase gene has been mutated.

In some cases, a nucleic acid can have a nucleotide sequence with at least about 75 percent sequence identity to a representative VInv nucleotide sequence. For example, a nucleotide sequence can have at least 75 percent, at least 80 percent, at least 85 percent, at least 90 percent, at least 91 percent, at least 92 percent, at least 93 percent, at least 94 percent, at least 95 percent, at least 96 percent, at least 97 percent, at least 98 percent, or at least 99 percent sequence identity to a representative, naturally occurring VInv nucleotide sequence.

In some cases, a mutation can be at a target sequence as set forth in a VInv sequence as set forth here (e.g., SEQ ID NO:1 or SEQ ID NO:27), or at a target sequence that is at least 95 percent (e.g., at least 96 percent, at least 97 percent, at least 98 percent, or at least 99 percent) identical to the sequence set forth in a VInv sequence as set forth here (e.g., SEQ ID NO:1 or SEQ ID NO:27).

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q−1 -r 2.

To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 120 matches when aligned with the sequence set forth in SEQ ID NO:1 is 86.3 percent identical to the sequence set forth in SEQ ID NO:1 (i.e., 120÷139×100=86.3). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Methods for selecting endogenous target sequences and generating TALE-nucleases targeted to such sequences can be performed as described elsewhere. See, for example, PCT Publication No. WO 2011/072246, which is incorporated herein by reference in its entirety. In some embodiments, software that specifically identifies TALE-nuclease recognition sites, such as TALE-NT 2.0 (Doyle et al., *Nucleic Acids Res* 40:W117-122, 2012) can be used.

Transcription activator-like (TAL) effectors are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104:10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (i.e., double-stranded breaks) in DNA can induce mutations into the wild type DNA sequence via NHEJ or homologous recombination, for example. In some cases, TALE-nucleases can be used to facilitate site directed mutagenesis in complex genomes, knocking out or otherwise altering gene function with great precision and high efficiency. As described in the Examples below, TALE-nucleases targeted to the *S. tuberosum* VInv gene can be used to mutagenize the endogenous gene, resulting in plants without detectable expression of VInv. The fact that some endonucleases (e.g., FokI) function as dimers can be used to enhance the target specificity of the TALE-nuclease. For example, in some cases a pair of TALE-nuclease monomers targeted to different DNA sequences (e.g., the underlined target sequences shown in FIG. 1) can be used. When the two TALE-nuclease recognition sites are in close proximity, as depicted in FIG. 1, the inactive monomers can come together to create a functional enzyme that cleaves the DNA. By requiring DNA binding to activate the nuclease, a highly site-specific restriction enzyme can be created.

Methods for using TALE-nucleases to generate potato plants, plant cells, or plant parts having mutations in endogenous genes include, for example, those described in the Examples herein. For example, one or more nucleic acids encoding TALE-nucleases targeted to selected VInv sequences (e.g., the VInv sequences shown in FIG. 1) can be transformed into plant cells (e.g., protoplasts), where they can be expressed. In some cases, one or more TALE-nuclease proteins can be introduced into plant cells (e.g., protoplasts). The cells, or a plant cell line or plant part generated from the cells, can subsequently be analyzed to determine whether mutations have been introduced at the target site(s), through nucleic acid-based assays or protein-based assays to detect expression levels as described above, for example, or using nucleic acid-based assays (e.g., PCR and DNA sequencing, or PCR followed by a T7E1 assay; Mussolino et al., *Nucleic Acids Res.* 39:9283-9293, 2011) to detect mutations at the genomic loci. In a T7E1 assay, genomic DNA can be isolated from pooled calli, and sequences flanking TALE-nuclease recognition sites for VInv can be PCR-amplified. Amplification products then can be denatured and re-annealed. If the re-annealed fragments form a heteroduplex, T7 endonuclease I cuts at the site of mismatch. The digested products can be visualized by gel electrophoresis to quantify mutagenesis activity of the TALE-nuclease.

More recently, a new genome engineering tool has been developed based on the RNA-guided Cas9 nuclease from the type II prokaryotic CRISPR (Clustered Regularly Interspaced Short palindromic Repeats) adaptive immune system (see, e.g., Belahj et al., *Plant Methods* 9:39, 2013). This system allows for cleaving DNA sequences that are flanked by a short sequence motif, referred as proto-spacer adjacent motif (PAM). Cleavage is achieved by engineering a specific crRNA that is complementary to the target sequence, which associates into the living cell with the endonuclease Cas9 from *S. pyogenes* that is heterologously expressed. In the crRNA/Cas9 complex, a dual tracrRNA:crRNA structure acts as guide RNA that directs the endonuclease Cas9 to the cognate target sequence. Since there are several PAM motifs present in the nucleotide sequence of the Vinv gene, crRNA specific to Vinv gene may be designed to introduce mutations or to inactivate all or part of the Vinv gene alleles within *Solanum* plant cells in which the Cas9 endonuclease and the crRNA are transfected and expressed. This approach can be used as an alternative to TALE-nucleases in some instances, to obtain the plants as described herein.

This document also encompasses further mutations that could be introduced in other *Solanum* genes so as to, for example:
- provide further acrylamide reduction by modifying the expression of genes involved in asparagine synthesis;
- prevent black spot bruise by reducing polyphenol oxidase-5 expression;
- prevent Potato Virus Y by reducing eIF4E gene expression;
- prevent late blight; or
- improve nematode, herbicide, or insect resistance.

Thus, the methods provided herein can be used to obtain gene stacking in a *Solanum* trait.

This disclosure also provides methods for producing food products using potato plant varieties with reduced CIS, as well as food products made by such methods. The methods provided herein can include, for example, providing or making *S. tuberosum* plants or plant parts that contain a TALE-nuclease-induced mutation in two or more endogenous VInv alleles and that have been subjected to cold storage, and using standard cooking and/or manufacturing methods to produce a food product (including, without limitation, potato chips, French fries, potato flakes, and mashed potatoes) from the plants or plant parts. In some embodiments, the reduced CIS can be observed as a reduction in bitterness and/or dark-pigmentation as compared to the bitterness and/or pigmentation observed in food products made from control plants or plant parts that do not contain the mutated VInv alleles and that have been subjected to cold storage. In some embodiments, the food products (e.g., food products made using methods that include cooking the plants or plant parts) can have reduced acrylamide levels as compared to the levels of acrylamide in food products made from *S. tuberosum* plants or plant parts that do not have mutations in the endogenous VInv alleles and that have been subjected to cold storage (e.g., prior to cooking). In some cases, the food products can have levels of acrylamide that are comparable to the levels of acrylamide in food products made from *S. tuberosum* plants or plant parts that were not subjected to cold storage.

The invention will be further described in the following examples, which do not limit the scope of the invention described in the claims.

EXAMPLES

Example 1—Engineering Sequence-Specific Nucleases to Mutagenize the VInv Gene

To completely inactivate or knock-out the alleles of the VInv gene in *S. tuberosum*, sequence-specific nucleases were designed that target the protein coding region in the vicinity of the start codon. Three TALE-nuclease pairs were designed to target the VInv gene family within the first 200 bp of the coding sequence using software that specifically identifies TALE-nuclease recognition sites. The TALE-nuclease recognition sites for the VInv genes are underlined in FIG. 1 and are listed in Table 1. TALE-nucleases were synthesized using methods similar to those described elsewhere (Cermak et al., *Nucleic Acids Res.* 39:e82, 2011; Reyon et al., *Nat. Biotechnol.* 30:460-465, 2012; and Zhang et al., *Nat. Biotechnol.* 29:149-153, 2011).

Example 2—VInv TALE-Nuclease Activity in Yeast

To assess the activity of the TALE-nucleases targeting the VInv gene, activity assays were performed in yeast by methods similar to those described elsewhere (Christian et al., *Genetics* 186:757-761, 2010). For these assays, a target plasmid was constructed with the TALE-nuclease recognition site cloned in a non-functional β-galactosidase reporter gene. The target site was flanked by a direct repeat of β-galactosidase coding sequence such that if the reporter gene was cleaved by the TALE-nuclease, recombination would occur between the direct repeats and function would be restored to the β-galactosidase gene. β-galactosidase activity, therefore, served as a measure of TALE-nuclease cleavage activity.

In the yeast assay, all of the VInv TALE-nuclease pairs (VInv_T01, VInv_T02 and VInv_T03) exhibited high cleavage activity under two distinct temperature conditions (i.e., 37° C. and 30° C.). Cleavage activities were normalized to the benchmark nuclease, I-SceI. Results are summarized in Table 2.

Example 3—Activity of VInv TALE-Nucleases at their Endogenous Target Sites in *S. tuberosum*

TALE-nuclease activity at endogenous target sites in *S. tuberosum* was measured by expressing the TALE-nucleases in protoplasts and surveying the TALE-nuclease target sites for mutations introduced by NHEJ. Methods for protoplast preparation were performed as described elsewhere (Shepard, in: *Genetic Improvement of Crops/Emergent Techniques* (pp. 185-219), Rubenstein, Gengenbach, Philips, and Green (Eds.), Univ. of Minnesota Press, Minneapolis, Minn., 1980; and Shepard and Totten, *Plant Physiol.* 60:313-316, 1977). Briefly, *S. tuberosum* mini tubers were planted in moistened vermiculite and grown under low light conditions for 3-5 weeks. Young, fully expanded leaves were collected and surface sterilized, and protoplasts were isolated.

TALE-nuclease-encoding plasmids, together with a YFP-encoding plasmid, were introduced into *S. tuberosum* protoplasts by PEG-mediated transformation as described elsewhere (Yoo et al., *Nature Protocols* 2:1565-1572, 2007). Twenty-four hours after treatment, transformation efficiency was measured by evaluating an aliquot of the transformed protoplasts using a fluorescent microscope to monitor YFP fluorescence. The remainder of the transformed protoplasts was harvested, and genomic DNA was prepared using a CTAB-based method. Using genomic DNA prepared from the protoplasts as a template, a 272-bp fragment encompassing the TALE-nuclease recognition site was amplified by PCR. Allele types were analyzed by individual clonal direct sequencing and 454 gyro-sequencing. Sequencing reads with indel mutations in the spacer region were considered as having been derived from imprecise repair of a cleaved TALE-nuclease recognition site by NHEJ. Mutagenesis frequency was calculated as the number of sequencing reads with NHEJ mutations out of the total sequencing reads. The values were then normalized by the transformation efficiency.

The activity of the VInv TALE-nuclease pairs, VInv_T01, VInv_T02 and VInv_T03, against their target gene is summarized in Table 3. The TALE-nucleases induced NHEJ mutations in VInvT1, VInvT2, and VInvT3, ranging from 3.6% to 9.5%. Examples of TALE-nuclease-induced mutations in VInvT1, VInvT2, and VInvT3 are shown in FIG. 2.

Example 4—Regeneration of *S. tuberosum* Lines with TALE-Nuclease-Induced Mutations in VInv

*S. tuberosum* lines were created with mutations in one or more alleles of the VInv gene. Protoplasts were isolated from surface sterilized leaves, and transformed with plasmids encoding one of the following: (i) TALE-nuclease VInv_T01 (ii) TALE-nuclease VInv_T02; (iii) TALE-nuclease VInv_T03: or (iv) YFP. Transformation efficiencies were monitored by the delivery of the YFP plasmid, which is visualized using a fluorescent microscope or by flow cytometry.

After PEG-mediated transformation, protoplasts were cultured using methods and media described elsewhere (Gamborg et al., in: *Plant Tissue Culture Methods and Applications in Agriculture* (pp. 115-153), Thorpe (Ed.), Academic Press, Inc., New York, N.Y., 1981), with slight modifications. Protoplasts were re-suspended in liquid plating medium at a cell density of $1 \times 10^5$/ml in a small petri dish, and stored at 25° C. in the dark. At day 14 after transformation, when the majority of the protoplasts had divided at least once, the protoplast culture was diluted two-fold in a suspension of P.-medium. At day 28 after transformation, the protoplast cultures were plated on a solid reservoir (10 ml) of CUL medium (Haberlach et al., *Plant Science* 39:67-74, 1985). At this point, protoplast-derived calli were visible to the eye.

At day 65 after transformation, protoplast-derived calli identified as mutants (e.g., using methods as described in Example 5) were transferred to a solid reservoir of DIF medium (Haberlach et al., supra). Calli were transferred to fresh DIF medium at biweekly intervals. As shoots formed, they were excised and placed into a solid reservoir of R.-medium (Gamborg et al., supra). These individual calli were transferred to shoot-inducing medium. Once roots formed, they were transferred to soil and grown to maturity for tuber production.

Example 5—Verification of S. tuberosum Lines with TALE-Nuclease-Induced Mutations in VInv S. tuberosum lines with mutations in all alleles of the VInv gene were assessed one month after transformation. Plants with putative mutations in the VInv gene were verified by PCR amplification of the target locus, and subsequently sequenced. FIG. 4 shows the mutations recovered in all alleles of a single plant, designated St116_1. Whereas potato is a tetraploid, it has been documented that many loci have three or fewer alleles (Draffehn et al., *BMC Plant Biol.* 10:271, 2010). In the cultivar "Ranger Russett," which was used in these experiments, only the three wild type alleles were identified (SEQ ID NOS:28, 29, and 30; FIG. 3). The mutations carried by plant St116_1 are set forth in SEQ ID NOS:32, 33, and 34, and have 4 bp, 4 bp and 17 bp deletions, respectively.

Example 6—Mutant S. tuberosum Lines have Desired Phenotypes

VInv transcript quantification is determined using quantitative real-time PCR of cDNA generated from mutant and control tuber mRNA extracts (Bhaskar et al., *Plant Physiol.* 154(2):939-948, 2010). The reduction of VInv expression is quantified using the comparative cycle threshold method described elsewhere (Livak and Schmittgen, *Method. Methods* 25:402-408, 2001). To assess acrylamide levels, potato chips are processed from cold-stored tubers without reconditioning. Potato tubers are cut axially to obtain slices and fried in vegetable oil for 2 minutes at 187° C. or until the cessation of bubbles. Fried chips are allowed to cool at room temperature (22° C.) for 5 to 8 minutes and are ground thoroughly with a mortar and pestle, and the powder is used for acrylamide analysis using methods described elsewhere (Bhaskar et al., supra). To assess changes in sugar composition in tubers after cold storage, a colorimetric glucose assay is employed using previously validated methods (Bethke and Busse, *Am. J. Potato Res.* 85:414-421, 2008).

TABLE 1

TALE-nuclease target sequences

| Gene | Target Sequence Left | SEQ ID NO: | Target Sequence Right | SEQ ID NO: |
|---|---|---|---|---|
| Vinv_T1 | TTCCTCCCGGATCAACC | 18 | GAAGTCCCTTAAAATCA | 19 |
| VInv_T2 | TTCCTCTCCTCTTTCCT | 20 | CTTCTTTCCGATCCTCA | 21 |
| Vinv_T3 | TAGCCTTCTTTCCGATC | 22 | CCGGACTTGCAGAGTAA | 23 |

TABLE 2

VInv TALE-nuclease activity in yeast

| TALE-nuclease Pair Name | TALE-nuclease Target Sequence | SEQ ID NO: | Activity in Yeast* | |
|---|---|---|---|---|
| | | | 37° C. | 30° C. |
| VInv_T01 | TTCCTCCCGGATCAACCC GATTCCGGCCACCGGAAG TCCCTTAAAATCA | 24 | 0.94 | 0.95 |
| VInv_T02 | TTCCTCTCCTCTTTCCTT TTGCTTTCTGTAGCCTTC TTTCCGATCCTCA | 25 | 0.92 | 0.89 |
| VInv_T03 | TAGCCTTCTTTCCGATCC TCAACAACCAGTCACCGG ACTTGCAGAGTAA | 26 | 0.96 | 0.82 |

*Normalized to I-SceI (max = 1.0)

TABLE 3

454 Pyro-Sequencing Data for VInv TALE-nuclease

| TALE-nuclease name | Location of target site | NHEJ mutagenesis freq. with TALE-nuclease* |
|---|---|---|
| VInv_T01 | VInvT1 | 3.6% (4614) |
| VInv_T02 | VInvT2 | 9.5% (4957) |
| VInv_T03 | VInvT3 | 9.9% (3350) |

*The total number of 454 sequencing reads used for this analysis was indicated in parentheses.

TABLE 4

S. tubersoum VInv complete CDS; GenBank
JN661860; SEQ ID NO: 27)

ATGGCCACGCAGTACCATTCCAGTTATGACCCGGAAAACTCCGCCTCCC
ATTACACATTCCTCCCGGATCAACCCGATTCCGGCCACCGGAAGTCCCT
TAAAATCATCTCCGGCATTTTCCTCTCCTCTTTCCTTTTGCTTTCTGTA
GCCTTCTTTCCGATCCTCAACAACCAGTCACCGGACTTGCAGAGTAACT
CCCGTTCGCCGGCGCCGCCGTCAAGAGGTGTTTCTCAGGGAGTCTCCGA
TAAGACTTTTCGAGATGTCGTCAATGCTAGTCACGTTTCTTATGCGTGG
TCCAATGCTATGCTTAGCTGGCAAAGAACTGCTTACCATTTTCAACCTC
AAAAAAATTGGATGAACGATCCTAATGGTCCATTGTACCACAAGGGATG
GTATCATCTTTTTTATCAATACAATCCAGATTCAGCTATTTGGGGAAAT
ATCACATGGGCCATGCCGTATCCAAGGACTTGATCCACTGGCTCTACT
TGCCTTTTGCCATGGTTCCTGATCAATGGTACGATATTAACGGTGTCTG
GACTGGGTCCGCTACCATCCTACCCGATGGTCAGATCATGATGCTTTAT
ACCGGTGACACTGATGATTATGTGCAAGTGCAAAATCTTGCGTACCCCA
CCAACTTATCTGATCCTCTCCTTCTAGACTGGGTCAAGTACAAAGGCAA
CCCGGTTCTGGTTCCTCCACCCGGCATTGGTGTCAAGGACTTTAGAGAC
CCGACCACTGCTTGGACCGGACCCCAAAATGGGCAATGGCTCTTAACAA
TCGGGTCTAAGATTGGTAAAACGGGTATTGCACTTGTTTATGAAACTTC
CAACTTCACAAGCTTTAAGCTATTGGATGAAGTGCTGCATGCGGTTCCG
GGTACGGGTATGTGGGAGTGTGTGGACTTTTACCCGGTATCGACTGAAA
AAACAAACGGGTTGGACACATCATATAACGGCCCGGGTGTAAAGCATGT
GTTAAAAGCAAGTTTAGATGACAATAAGCAAGATCACTATGCTATTGGG
ACGTATGACTTGACAAAGAACAAATGGACACCCGATAAGCCGGAATTGG
ATTGTGGAATTGGGTTGAAGCTGGATTATGGGAAATATTATGCATCAAA

TABLE 4-continued

S. tubersoum VInv complete CDS; GenBank
JN661860; SEQ ID NO: 27)

GACATTTTATGACCCGAAGAAACAACGAAGAGTACTGTGGGGATGGATT
GGGGAAACTGATAGTGAATCTGCTGACCTGCAGAAGGGATGGGCATCTG
TACAGAGTATTCCAAGGACAGTGCTTTACGACAAGAAGACAGGGACACA
TCTACTTCAGTGGCCAGTTGAAGAAATTGAAAGCTTAAGAGCGGGTGAT
CCTATTGTTAAGCAAGTCAATCTTCAACCAGGTTCAATTGAGCTACTCC
ATGTTGACTCAGCTGCAGAGTTGGATATAGAAGCCTCATTTGAAGTGGA
CAAAGTCGCGCTCCAGGGAATAATTGAAGCAGATCATGTAGGTTTCAGC
TGCTCTACTAGTGGAGGTGCTGCTAGCAGAGGCATTTTGGGACCATTTG
GTGTCGTTGTAATTGCTGATCAAACGCTATCTGAGCTAACGCCAGTTTA
CTTCTTCATTTCTAAAGGAGCTGATGGTCGAGCTGAGACTCACTTCTGT
GCTGATCAAACTAGATCCTCAGAGGCTCCGGGAGTTGCTAAACGAGTTT
ATGGTAGTTCAGTACCCGTGTTGGACGGTGAAAAACATTCGATGAGATT
ATTGGTGGACCACTCAATTGTGGAGAGCTTTGCTCAAGGAGGAAGAACA
GTCATAACATCGCGAATTTACCCAACAAAGGCAGTGAATGGAGCAGCAC
GACTCTTCGTTTTCAATAATGCCACAGGGGCTAGCGTGACTGCCTCCGT
CAAGATTTGGTCACTTGAGTCGGCTAATATTCGATCCTTCCCCTTGCAA
GACTTGTAA

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A *Solanum tuberosum* plant, plant part, or plant cell comprising a deletion in at least two vacuolar invertase (VInv) alleles endogenous to said plant, plant part, or plant cell, wherein said deletion was induced by introducing one or more rare-cutting endonucleases into a *S. tuberosum* cell, such that said plant, plant part, or plant cell has reduced expression of VInv as compared to a control *S. tuberosum* plant, plant part, or plant cell that lacks said deletion, and wherein said deletion is at a target sequence as set forth in SEQ ID NO:1, or at a target sequence having at least 95% identity to SEQ ID NO:1, and wherein each of said at least two VInv alleles having a deletion comprises the sequence set forth in SEQ ID NO:32, SEQ ID NO:33, or SEQ ID NO:34.

2. The plant, plant part, or plant cell of claim 1, wherein at least three VInv alleles comprise a deletion of more than one nucleotide base pair, and wherein each of the at least three VInv alleles comprises the sequence set forth in SEQ ID NO:32, SEQ ID NO:33, or SEQ ID NO:34.

3. A method for making a *Solanum tuberosum* plant that has reduced cold-induced sweetening, wherein said method comprises:

(a) contacting a population of *S. tuberosum* plant cells comprising a functional VInv allele with one or more rare-cutting endonucleases targeted to one or more endogenous VInv sequences, wherein said one or more rare-cutting endonucleases are targeted to a sequence within SEQ ID NO:1 or within a sequence having at least 95% identity to the sequence set forth in SEQ ID NO:1, (b) selecting, from said population, a cell in which at least two VInv alleles have been inactivated, and (c) growing said selected plant cell into a *S. tuberosum* plant, wherein said *S. tuberosum* plant has reduced cold-induced sweetening as compared to a control *S. tuberosum* plant in which said VInv alleles have not been inactivated, and wherein each of said at least two VInv alleles having a deletion comprises the sequence set forth in SEQ ID NO:32, SEQ ID NO:33, or SEQ ID NO:34.

4. The method of claim 3, wherein at least three VInv alleles comprise a deletion of more than one nucleotide base pair, and wherein each of the at least three VInv alleles comprises the sequence set forth in SEQ ID NO:32, SEQ ID NO:33, or SEQ ID NO:34.

5. A method for producing a food product, comprising:
(a) providing a *S. tuberosum* plant or plant part that (i) comprises a deletion in at least two VInv alleles endogenous to said plant or plant part, wherein each said deletion is at a target sequence as set forth in SEQ ID NO:1, or at a target sequence having at least 95% identity to SEQ ID NO:1, wherein said deletion was induced by introducing one or more rare-cutting endonucleases into a *S. tuberosum* cell, such that said plant, plant part, or plant cell has reduced expression of VInv as compared to a control *S. tuberosum* plant or plant part that lacks said deletion, and (ii) has been subjected to cold storage; and
(b) producing a food product from said plant or plant part, wherein each of said at least two VInv alleles having a deletion comprises the sequence set forth in SEQ ID NO:32, SEQ ID NO:33, or SEQ ID NO:34.

6. The method of claim 5, wherein at least three VInv alleles comprise a deletion of more than one nucleotide base pair, and wherein each of the at least three VInv alleles comprises the sequence set forth in SEQ ID NO:32, SEQ ID NO:33, or SEQ ID NO:34.

* * * * *

SEQUENCE LISTING

<160> NUMBER OF SEQ ID NOS: 35

<210> SEQ ID NO 1
<211> LENGTH: 139
<212> TYPE: DNA
<213> ORGANISM: Solanum tuberosum

<400> SEQUENCE: 1
attcctcccg gatcaacccg attccggcca ccggaagtcc cttaaaatca tctccggcat      60
tttcctctcc tctttccttt tgctttctgt agccttcttt ccgatcctca acaaccagtc     120
accggacttg cagagtaac                                                   139

<210> SEQ ID NO 2
<211> LENGTH: 49
<212> TYPE: DNA
<213> ORGANISM: Solanum tuberosum

<400> SEQUENCE: 2
ttcctcccgg atcaacccga ttccggccac cggaagtccc ttaaaatca                  49

<210> SEQ ID NO 3
<211> LENGTH: 28
<212> TYPE: DNA
<213> ORGANISM: Artificial Sequence
<220> FEATURE:
<223> OTHER INFORMATION: mutant of Solanum tuberosum

<400> SEQUENCE: 3
ttcctcccgg atcaactccc ttaaatca                                28

<210> SEQ ID NO 4
<211> LENGTH: 39
<212> TYPE: DNA
<213> ORGANISM: Artificial Sequence
<220> FEATURE:
<223> OTHER INFORMATION: mutant of Solanum tuberosum

<400> SEQUENCE: 4
ttcctcccgg atcagccacc ggaaatccct taaaactca                    39

<210> SEQ ID NO 5
<211> LENGTH: 36
<212> TYPE: DNA
<213> ORGANISM: Artificial Sequence
<220> FEATURE:
<223> OTHER INFORMATION: mutant of Solanum tuberosum

<400> SEQUENCE: 5
ttcctcccgg atcaacccga ttgtcccta aaatca                        36

<210> SEQ ID NO 6
<211> LENGTH: 21
<212> TYPE: DNA
<213> ORGANISM: Artificial Sequence
<220> FEATURE:
<223> OTHER INFORMATION: mutant of Solanum tuberosum

<400> SEQUENCE: 6
ttcctcccgg atcaacccga t                                       21

<210> SEQ ID NO 7
<211> LENGTH: 27
<212> TYPE: DNA
<213> ORGANISM: Artificial Sequence
<220> FEATURE:
<223> OTHER INFORMATION: mutant of Solanum tuberosum

<400> SEQUENCE: 7
ttcctcccgg atcaacccga ttccggc                                 27

<210> SEQ ID NO 8
<211> LENGTH: 49
<212> TYPE: DNA
<213> ORGANISM: Solanum tuberosum

<400> SEQUENCE: 8
ttcctctcct ctttccttt gctttctgta gccttctttc cgatcctca           49

<210> SEQ ID NO 9
<211> LENGTH: 43
<212> TYPE: DNA
<213> ORGANISM: Artificial Sequence
<220> FEATURE:
<223> OTHER INFORMATION: mutant of Solanum tuberosum -continued

<400> SEQUENCE: 9
ttcctctcct ctttccttt gctagccttc tttccgatcc tca                    43

<210> SEQ ID NO 10
<211> LENGTH: 46
<212> TYPE: DNA
<213> ORGANISM: Artificial Sequence
<220> FEATURE:
<223> OTHER INFORMATION: mutant of Solanum tuberosum

<400> SEQUENCE: 10
ttcctctcct ctctccttt gcttttagtc ttctttccga tcctca                 46

<210> SEQ ID NO 11
<211> LENGTH: 45
<212> TYPE: DNA
<213> ORGANISM: Artificial Sequence
<220> FEATURE:
<223> OTHER INFORMATION: mutant of Solanum tuberosum

<400> SEQUENCE: 11
ttcctctcct ctttccttt gctgtagcct tctttccgat cctca                  45

<210> SEQ ID NO 12
<211> LENGTH: 44
<212> TYPE: DNA
<213> ORGANISM: Artificial Sequence
<220> FEATURE:
<223> OTHER INFORMATION: mutant of Solanum tuberosum

<400> SEQUENCE: 12
ttcctctcct ctttccttt gcgtagcctt ctttccgatc ctca                   44

<210> SEQ ID NO 13
<211> LENGTH: 49
<212> TYPE: DNA
<213> ORGANISM: Solanum tuberosum

<400> SEQUENCE: 13
tagccttctt tccgatcctc aacaaccagt caccggactt gcagagtaa             49

<210> SEQ ID NO 14
<211> LENGTH: 43
<212> TYPE: DNA
<213> ORGANISM: Artificial Sequence
<220> FEATURE:
<223> OTHER INFORMATION: mutant of Solanum tuberosum

<400> SEQUENCE: 14
tagccttctt tccgatcctc aacacaccgg acttgcagag taa                   43

<210> SEQ ID NO 15
<211> LENGTH: 44
<212> TYPE: DNA
<213> ORGANISM: Artificial Sequence
<220> FEATURE:
<223> OTHER INFORMATION: mutant of Solanum tuberosum

<400> SEQUENCE: 15
tagccttctt tccgatcctc aaagtcaccg gacttgcaga gtaa                  44

<210> SEQ ID NO 16
<211> LENGTH: 40
<212> TYPE: DNA
<213> ORGANISM: Artificial Sequence

```
<220> FEATURE:
<223> OTHER INFORMATION: mutant of Solanum tuberosum

<400> SEQUENCE: 16
tagccttctt tccgatcctc tcaccggact tgcagagtaa                    40

<210> SEQ ID NO 17
<211> LENGTH: 42
<212> TYPE: DNA
<213> ORGANISM: Artificial Sequence
<220> FEATURE:
<223> OTHER INFORMATION: mutant of Solanum tuberosum

<400> SEQUENCE: 17
tagccttctt tccgatcctc agtcaccgga cttgcagagt aa                 42

<210> SEQ ID NO 18
<211> LENGTH: 17
<212> TYPE: DNA
<213> ORGANISM: Solanum tuberosum

<400> SEQUENCE: 18
ttcctcccgg atcaacc                                             17

<210> SEQ ID NO 19
<211> LENGTH: 17
<212> TYPE: DNA
<213> ORGANISM: Solanum tuberosum

<400> SEQUENCE: 19
gaagtccctt aaaatca                                             17

<210> SEQ ID NO 20
<211> LENGTH: 17
<212> TYPE: DNA
<213> ORGANISM: Solanum tuberosum

<400> SEQUENCE: 20
ttcctctcct ctttcct                                             17

<210> SEQ ID NO 21
<211> LENGTH: 17
<212> TYPE: DNA
<213> ORGANISM: Solanum tuberosum

<400> SEQUENCE: 21
cttctttccg atcctca                                             17

<210> SEQ ID NO 22
<211> LENGTH: 17
<212> TYPE: DNA
<213> ORGANISM: Solanum tuberosum

<400> SEQUENCE: 22
tagccttctt tccgatc                                             17

<210> SEQ ID NO 23
<211> LENGTH: 17
<212> TYPE: DNA
<213> ORGANISM: Solanum tuberosum

<400> SEQUENCE: 23
ccggacttgc agagtaa                                             17
```

<210> SEQ ID NO 24
<211> LENGTH: 49
<212> TYPE: DNA
<213> ORGANISM: Solanum tuberosum

<400> SEQUENCE: 24
ttcctcccgg atcaacccga ttccggccac cggaagtccc ttaaaatca       49

<210> SEQ ID NO 25
<211> LENGTH: 49
<212> TYPE: DNA
<213> ORGANISM: Solanum tuberosum

<400> SEQUENCE: 25
ttcctctcct ctttcctttt gctttctgta gccttctttc cgatcctca       49

<210> SEQ ID NO 26
<211> LENGTH: 49
<212> TYPE: DNA
<213> ORGANISM: Solanum tuberosum

<400> SEQUENCE: 26
tagccttctt tccgatcctc aacaaccagt caccggactt gcagagtaa       49

<210> SEQ ID NO 27
<211> LENGTH: 1920
<212> TYPE: DNA
<213> ORGANISM: Solanum tuberosum

<400> SEQUENCE: 27
atggccacgc agtaccattc cagttatgac ccggaaaaact ccgcctccca ttacacattc     60
ctcccggatc aacccgattc cggcaccgg aagtccctta aaatcatctc cggcattttc      120
ctctcctctt cctttttgct ttctgtagcc ttctttccga tcctcaacaa ccagtcaccg     180
gacttgcaga gtaactcccg ttcgccggcg ccgccgtcaa gaggtgtttc tcagggagtc     240
tccgataaga cttttcgaga tgtcgtcaat gctagtcacg tttcttatgc gtggtccaat     300
gctatgctta gctggcaaag aactgcttac catttcaac ctcaaaaaaa ttggatgaac       360
gatcctaatg gtccattgta ccacaaggga tggtatcatc tttttttatca atacaatcca    420 gattcagcta tttggggaaa tatcacatgg ggccatgccg tatccaagga cttgatccac     480
tggctctact tgccttttgc catggttcct gatcaatggt acgatattaa cggtgtctgg     540
actgggtccg ctaccatcct acccgatggt cagatcatga tgctttatac cggtgacact     600
gatgattatg tgcaagtgca aaatcttgcg taccccacca acttatctga tcctctcctt     660
ctagactggg tcaagtacaa aggcaacccg gttctggttc ctccacccgg cattggtgtc     720
aaggacttta gagacccgac cactgcttgg accggacccc aaaatgggca atggctctta    780
acaatcgggt ctaagattgg taaaacgggt attgcacttg tttatgaaac ttccaacttc    840
acaagcttta agctattgga tgaagtgctg catgcgttc cgggtacggg tatgtgggag     900
tgtgtggact tttacccggt atcgactgaa aaaacaaacg ggttggacac atcatataac     960 ggccccgggtg taaagcatgt gttaaaagca agtttagatg acaataagca agatcactat    1020
gctattggga cgtatgactt gacaaagaac aaatggacac ccgataagcc ggaattggat     1080
tgtggaattg ggttgaagct ggattatggg aaatattatg catcaaagac attttatgac    1140
ccgaagaaac aacgaagagt actgtgggga tggattgggg aaactgatag tgaatctgct    1200
gacctgcaga agggatgggc atctgtacag agtattccaa ggacagtgct ttacgacaag    1260

```
aagacaggga cacatctact tcagtggcca gttgaagaaa ttgaaagctt aagagcgggt    1320
gatcctattg ttaagcaagt caatcttcaa ccaggttcaa ttgagctact ccatgttgac    1380
tcagctgcag agttggatat agaagcctca tttgaagtgg acaaagtcgc gctccaggga    1440
ataattgaag cagatcatgt aggtttcagc tgctctacta gtggaggtgc tgctagcaga    1500
ggcattttgg gaccatttgg tgtcgttgta attgctgatc aaacgctatc tgagctaacg    1560
ccagtttact tcttcatttc taaaggagct gatggtcgag ctgagactca cttctgtgct    1620
gatcaaacta gatcctcaga ggctccggga gttgctaaac gagtttatgg tagttcagta    1680
cccgtgttgg acggtgaaaa acattcgatg agattattgg tggaccactc aattgtggag    1740
agctttgctc aaggaggaag aacagtcata acatcgcgaa tttacccaac aaaggcagtg    1800
aatggagcag cacgactctt cgttttcaat aatgccacag gggctagcgt gactgcctcc    1860
gtcaagattt ggtcacttga gtcggctaat attcgatcct tccccttgca agacttgtaa    1920
```

<210> SEQ ID NO 28
<211> LENGTH: 230
<212> TYPE: DNA
<213> ORGANISM: Solanum tuberosum

<400> SEQUENCE: 28

```
atagctctcg cagttatgac ccggaaactc cgcctcccat tacacattcc tcccggatca     60
acctgattcc ggccaccgga agtcccttaa aatcatctcc ggcattttcc tctcctcttt    120
cctttgtctt tctgtagcct tctttccgat cctcaacaac cagtcaccgg acttgcagag    180
taactcccgt tcgccggcgc cgccgtcaag aggtgtttct cagggagtct               230
```

<210> SEQ ID NO 29
<211> LENGTH: 230
<212> TYPE: DNA
<213> ORGANISM: Solanum tuberosum

<400> SEQUENCE: 29

```
atagctctcg cagttatgac ccggaaactc cgcctcccat tacacattcc tcccggatca     60
acccgattcc ggccaccgga agtcccttaa aatcatctcc ggcattttcc tctcctcttt    120
cctttgtctt tctgtagcct tctttccgat cctcaacaac cagtcaccgg acttgcagag    180
taactcccgt tcgccggcgc cgccgtcaag aggtgtttct cagggagtct               230
```

<210> SEQ ID NO 30
<211> LENGTH: 230
<212> TYPE: DNA
<213> ORGANISM: Solanum tuberosum

<400> SEQUENCE: 30

```
atagctctcg cagttatgac ccggaaactc cgcctcccat tacacattcc tcccggatca     60
acacgattcc ggccaccgga aatcccttaa aatcatctcc ggcattttcc tctcctctct    120
cctttgtctt tctttatcct tctttccgat cctcaacaac cagtcaccgg acttgaaaag    180
taacgcccgt tcgccggcgc cgccgtcaag aggtgtttct cagggagtct               230
```

<210> SEQ ID NO 31
<211> LENGTH: 49
<212> TYPE: DNA
<213> ORGANISM: Solanum tuberosum

<400> SEQUENCE: 31

```
ttcctctcct ctctccttttt gctttcttta gtcttctttc cgatcctca          49

<210> SEQ ID NO 32
<211> LENGTH: 45
<212> TYPE: DNA
<213> ORGANISM: Artificial Sequence
<220> FEATURE:
<223> OTHER INFORMATION: mutant of Solanum tuberosum

<400> SEQUENCE: 32
ttcctctcct ctttccttttt gctgtagcct tctttccgat cctca              45

<210> SEQ ID NO 33
<211> LENGTH: 45
<212> TYPE: DNA
<213> ORGANISM: Artificial Sequence
<220> FEATURE:
<223> OTHER INFORMATION: mutant of Solanum tuberosum

<400> SEQUENCE: 33
ttcctctcct ctctccttttt gctttagtct tctttccgat cctca              45

<210> SEQ ID NO 34
<211> LENGTH: 32
<212> TYPE: DNA
<213> ORGANISM: Artificial Sequence
<220> FEATURE:
<223> OTHER INFORMATION: mutant of Solanum tuberosum

<400> SEQUENCE: 34
ttcctctcct ctagccttct ttccgatcct ca                             32

<210> SEQ ID NO 35
<211> LENGTH: 9
<212> TYPE: PRT
<213> ORGANISM: Artificial Sequence
<220> FEATURE:
<223> OTHER INFORMATION: consensus

<400> SEQUENCE: 35

Leu Ala Gly Leu Ile Asp Ala Asp Gly
1               5
```